(12) United States Patent
Thiele et al.

(10) Patent No.: US 6,544,999 B2
(45) Date of Patent: Apr. 8, 2003

(54) POLYMORPHS OF N-METHYL-N-(3-{3-[2-THIENYLCARBONYL]-PYRAZOL-[1,5-α]-PYRIMIDIN-9-YL}PHENYL)ACETAMIDE AND COMPOSITIONS AND METHODS RELATED THERETO

(75) Inventors: William J. Thiele, San Diego, CA (US); Patrick B. O'Donnell, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 09/982,524

(22) Filed: Oct. 16, 2001

(65) Prior Publication Data

US 2002/0107256 A1 Aug. 8, 2002

Related U.S. Application Data

(63) Continuation of application No. 09/654,447, filed on Sep. 1, 2000.
(60) Provisional application No. 60/304,205, filed on Oct. 19, 1999, and provisional application No. 60/229,352, filed on Sep. 2, 1999.

(51) Int. Cl.$^7$ .................. C07D 487/04; A61K 31/519; A61P 5/02
(52) U.S. Cl. ..................... 514/259.3; 544/281
(58) Field of Search ................ 544/281; 514/259.3

(56) References Cited

U.S. PATENT DOCUMENTS

| | | | |
|---|---|---|---|
| 4,382,938 A | 5/1983 | Kaplan et al. | 424/256 |
| 4,460,592 A | 7/1984 | Kaplan et al. | 424/256 |
| 4,521,422 A | 6/1985 | Dusza et al. | 514/258 |
| 4,626,538 A | 12/1986 | Dusza et al. | 514/258 |
| 4,654,347 A | 3/1987 | Dusza et al. | 514/258 |
| 4,794,185 A | 12/1988 | Rossey et al. | 546/121 |
| 4,808,594 A | 2/1989 | George et al. | 514/300 |
| 4,847,256 A | 7/1989 | Tseng et al. | 514/258 |
| 4,900,836 A | 2/1990 | Tomcufcik et al. | 546/279 |
| 5,538,977 A | 7/1996 | Dusza et al. | 514/258 |
| 5,714,607 A | 2/1998 | Padmanathan | 544/281 |
| 5,891,891 A | 4/1999 | Benincasa | 514/300 |

FOREIGN PATENT DOCUMENTS

WO   WO 99/57101   11/1999

OTHER PUBLICATIONS

Cato et al., "Brochure for Clinical Investigators–Sedative Hypnotic Compound CL 285,489," Cato Research Limited, Study Code 34060–033, Project Report No. 34060–CIB, Apr. 25, 1990.

Niphadkar, "Predevelopment Studies on Sedative/Hypnotic Compound, CL 285,489," Medical Research Division Formal Laboratory Report, Oct. 3, 1989.

Foster, "Developments in CNS Drugs II: Drugs of Tomorrow," Smi Conference, London, UK, May 11–12, 1999.

Brittain, Harry G., (ed.), *Polymorphism in Pharmaceutical*, Marcel Dekker, Inc., New York, 1999, Chapter 3, "Structural Aspects of Pholmorphism," pp. 73–124.

Brittain, Harry G., (ed.), *Polymorphism in Pharmaceutical*, Marcel Dekker, Inc., New York, 1999, Chapter 5, "Generation of Pholmorphs, Hydrates, Solvates, and Amorphous Solids," pp. 183–226.

Brittain, Harry G., (ed.), *Polymorphism in Pharmaceutical*, Marcel Dekker, Inc., New York, 1999, Chapter 7, "Effects of Polymorphism and Solid–State Solvation on Solubility and Dissolution Rate," pp. 279–330.

Brittain, Harry G., (ed.), *Polymorphism in Pharmaceutical*, Marcel Dekker, Inc., New York, 1999, Chapter 8, "Effects of Pharmaceutical Processing on Drug Polymorphs and Solvates," pp. 331–361.

*Primary Examiner*—Mark L. Berch
*Assistant Examiner*—Tamthom N. Truong
(74) *Attorney, Agent, or Firm*—Seed IP Law Group PLLC

(57) ABSTRACT

Polymorphs of N-methyl-N-(3-{3-[2-thienylcarbonyl]-pyrazol-[1,5-α]-pyrimidin-7-yl}phenyl)acetamide (Compound 1), and use of the same as a sedative-hypnotic, anxiolytic, anticonvulsant, and skeletal muscle relaxant agent. Processes for making the same, as well as related compositions and methods are also disclosed, particularly with regard to treatment of insomnia. A polymorph Form I possessing exception physical and heat stability is provided. A polymorph Form II

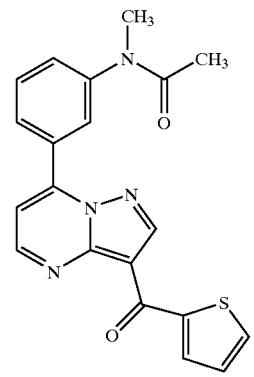

15 Claims, 5 Drawing Sheets

POLYMORPHS OF N-METHYL-N-(3-{3-[2-THIENYLCARBONYL]-PYRAZOL-[1,5-α]-PYRIMIDIN-9-YL}PHENYL)ACETAMIDE AND COMPOSITIONS AND METHODS RELATED THERETO

CROSS-REFERENCE TO RELATED APPLICATIONS

This application is a continuation of U.S. patent application No. 09/654,447 filed Sep. 1, 2000; and claims the benefit of U.S. Provisional Application 60/304,205 filed Oct. 19, 1999; and claims the benefit of U.S. Provisional Application No. 60/229,352 filed Sep. 2, 1999.

FIELD OF THE INVENTION

This invention is directed to polymorphs of N-methyl-N-(3-{3-[2-thienylcarbonyl]-pyrazol-[1,5-α]-pyrimidin-7-yl}phenyl)acetamide having activity over a wide range of indications, and particularly usefull for the treatment of insomnia, and to related processes, compositions and methods.

BACKGROUND OF THE INVENTION

The term "insomnia" is used to describe all conditions related to the perception of inadequate or non-restful sleep by the patient (Dement, *International Pharmacopsychiatry* 17:3–38, 1982). Insomnia is the most frequent complaint, being reported by 32% of the adult population surveyed in the Los Angeles area (Bixler et al, *Amer. Journal of Psychiatry* 136:1257–1262, 1979), and 13% of the population surveyed in San Marino, Italy (Lugaresi et al., *Psychiatric Annals* 17:446–453, 1987). Fully 45% of the surveyed adult population of Alachua County, Fla., reported trouble getting to sleep or staying asleep (Karacan et al., *Social Science and Medicine* 10:239–244, 1976). The prevalence of insomnia has also been shown to be related to the age and sex of the individuals, being higher in older individuals and in females.

Insomnia, left untreated, may result in disturbances in metabolism and overall body function. Reduced productivity and significant changes in mood, behavior and psychomotor function. Chronic insomnia is associated with a higher incidence of morbidity and mortality. Traditionally, the management of insomnia includes treatment and/or mitigation of the etiological factors, improving sleep hygiene and the administration of hypnotic agents. The early hypnotic agents, such as barbiturates, while effective, elicited a spectrum of unwanted side effects and longer-term complications. For example, barbiturates have the potential to result in lethargy, confusion, depression and a variety of other residual effects many hours post dosing, as well as having a potential for being highly addictive.

During the 1980's, the pharmaceutical treatment of insomnia shifted away from barbiturates and other CNS depressants toward the benzodiazepine class of sedative-hypnotics. This class of sedative-hypnotic agents showed substantial effectiveness in producing a calming effect which results in sleep-like states in man and animals (Gee et al., *Drugs in Central Nervous Systems*, Horwell (ed.), New York, Marcel Dekker, Inc., 1985, p. 123–147) and had a greater safety margin than prior hypnotics, barbiturates or chloral hydrate (Cook and Sepinwall, *Mechanism of Action of Benzodiazepines*, Costa and Greengard (eds.), New York, Raven Press, 1975, p. 1–28). The therapeutic action of benzodiazepines is believed to be mediated by binding to a specific receptor on benzodiazepine GABA complexes in the brain. As a result of this binding, synaptic transmission is altered at neurons containing the benzodiazepine GABA complex (Clody et al., *Benzodiazepines II*, Rechtschaffen and Kales (eds.), New York, Springer-Verlag, 1989, p. 341–354). The clinical usefulness of different benzodiazepine hypnotics relates largely to their pharmacokinetic differences with regard to this binding and, in particular, to the half-lives of the parent compound and its active metabolites (Finkle, *Benzodiazepines II*, Rechtschaffen and Kales (eds.), New York, Springer-Verlag, 1989, p. 619–628).

As with barbiturates, however, many benzodiazepines also possess side effects that limit their usefulness in certain patient populations. These problems include synergy with other CNS depressants (especially alcohol), the development of tolerance upon repeat dosing, rebound insomnia following discontinuation of dosing, hangover effects the next day, and impairment of psychomotor performance and memory (Cook and Sepinwall, supra; Hartman, *Benzodiazepines II*, Rechtschaffen and Kales (eds.), New York, Springer-Verlag, 1989, p. 187–198; Linnoila and Ellinwood, *Benzodiazepines*, Rechtschaffen and Kales (eds.), New York, Springer-Verlag, 1989, p. 601–618). Memory impairment, which can include amnesia for events occurring prior to and after drug administration, is of particular concern in the elderly whose cognitive function may already be impaired by the aging process (Ayd, *Benzodiazepines*, Rechtschaffen and Kales (eds.), New York, Springer-Verlag, 1989, p. 593–600; Finkle, supra; Linnoila and Ellinwood, supra).

More recently, a new class of agents have undergone development. These agents are non-benzodiazepine compounds, which being selectively to a specific receptor subtype of the benzodiazepine receptor. This receptor selectivity is thought to be the mechanism by which these compounds are able to exert a robust hypnotic effect, while also demonstrating an improved safety profile relative to the non-selective, benzodiazepine class of agents. The first of these agents to be approved by the United States Food and Drug Administration (FDA) for marketing in the United States was Ambien (zolpidem tartrate), which is based on the imidazopyridine backbone (see U.S. Pat. Nos. 4,382,938 and 4,460,592). In addition to Ambien, another compound known as Sonata (zaleplon), which is a pyrazolopyrimidine-based compound, recently received FDA approval (see U.S. Pat. No. 4,626,538). Other non-benzodiazepine compounds and/or methods for making or using the same have also been reported (see, e.g., U.S. Pat. Nos. 4,794,185, 4,808,594, 4,847,256, 5,714,607, 4,654,347, 5,891,891).

While significant advances have been made in this field, there is still a need in the art for compounds that are effective as sedative or hypnotic agents generally. particularly in the context of treating insomnia One such class of compound is disclosed in U.S. Pat. Nos. 4,521,422 and 4,900,836. These patents, particularly U.S. Pat. No. 4,521,422, disclose a genus encompassing certain aryl and heteroaryl[7-(aryl and heteroaryl)-pyrazolo[1,5-a]pyrimidin-3-yl]methanones. More specifically, U.S. Pat. No. 4,521,422 discloses that compounds of this genus may be made by reacting an appropriately substituted pyrazole (a) with an appropriately substituted 3-dimethylamino-2-propen-1-one (b).

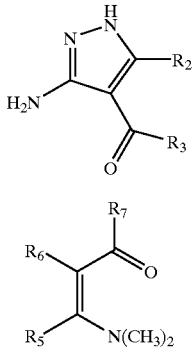

(a)

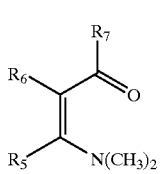

(b)

One particular compound that falls within the genus of U.S. Pat. No. 4,521,422 is N-methyl-N-(3-{3-[2-thienylcarbonyl]-pyrazol-[1,5-α]-pyrimidin-7-yl}phenyl)acetamide, which has the following structure 1 (referred to herein as "Compound 1"):

Compound 1

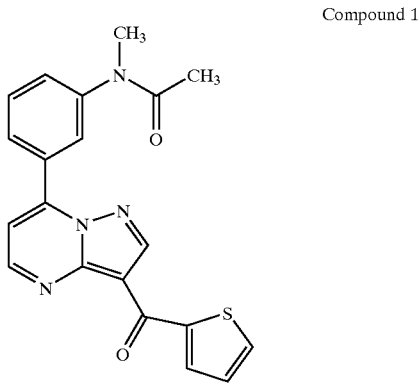

Compound 1 may be made according to the procedures disclosed in U.S. Pat. No. 4,521,422, which procedure is more specifically disclosed in Example 1. In short, Compound 1 is made by reacting an appropriately substituted pyrazole (a) (i.e., wherein $R_2$ is hydrogen and $R_3$ is 2-thienyl) with an appropriately substituted 3-dimethylamino-2-propen-1-one (b) (i.e., wherein $R_5$ and $R_6$ are hydrogen and $R_7$ is 3-N(CH$_3$)(COCH$_3$)phenyl), followed by recystallization from dichloromethane/hexane. As one skilled in this field will recognize, the dichloromethane has been used to selectively solubilize or extract Compound 1 away from unwanted impurities, while subsequent addition of hexane causes Compound 1 to crystallize or "crash out." When made in this manner, Compound 1 exists as a mixture of polymorphs.

While Compound 1 has proven particularly promising for the treatment of insomnia, improved forms of this compound are desired, particularly with regard to enhanced solubility, oral bioavailability and/or physical stability. The present invention fulfills this need and provides further related advantages.

SUMMARY OF THE INVENTION

The present invention is directed to substantially pure polymorphs of Compound 1 (referred to herein as "Form I" and "Form II") which have particularly advantageous properties.

A substantially pure polymorph Form I of Compound 1 exhibits a predominant endotherm at about 196° C. (192–197° C. as measured by a TA 2920 Modulated Differential Scanning Calorimeter (DSC) at a scan rate of 10° C. per minute), and contains less than about 6% by weight of Form II. Specific embodiments of the substantially pure polymorph Form I contain less than about 2% by weight total impurities, less than about 1% by weight water, and/or less than about 0.5% by weight residual organic solvent. Another embodiment includes substantially pure polymorph Form I containing less than 1% by weight total impurities, less than about 0.75% by weight water, and less than about 0.4% by weight residual organic solvent. Other embodiments of the polymorph Form I are described further below.

A substantially pure polymorph Form II of Compound 1 exhibits a predominant endotherm at about 176° C. (173–177° C. as measured by a TA 2920 Modulated Differential Scanning Calorimeter at a scan rate of 10° C. per minute), and contains less than about 20% by weight of Form I. Specific embodiments of the substantially pure polymorph Form II contain less than about 2% by weight total impurities, less than about 1% by weight water, and less than about 0.5% by weight residual organic solvent. Another embodiment includes substantially pure polymorph Form II containing less than 1% by weight total impurities, less than about 0.75% by weight water, and less than about 0.4% by weight residual organic solvent. Other embodiments of the polymorph Form II are described further below, The polymorphs Form I and II are useful as sedative or hypnotic agents generally and, more specifically, are useful in the treatment of insomnia. Thus, the present invention is also directed to methods for treating a variety of conditions by administering an effective amount of the polymorph Form I and/or II to an animal or subject in need thereof (referred to herein as a "patient"), typically a warm-blooded animal (including a human). Prior to administration, the administered polymorph is generally formulated as a pharmaceutical composition that contains an effective dosage amount of the polymorph in combination with one (or more) pharmaceutically acceptable carrier(s).

Conditions that may be treated by the polymorphs of this invention, or a pharmaceutical composition containing a polymorph of this invention, include any disorder or disease that may be improved or ameliorated by administration of a polymorph according to the invention, which possess anxiolytic, anti-anoxic, sleep-inducing, hypnotic, anticonvulsant, and/or skeletal muscle relaxant properties. Such conditions include insomnia specifically, as well as sleep disorders generally and other neurological and psychiatric complaints; anxiety states; vigilance disorders, such as for combating behavioral disorders attributable to cerebral vascular damage and to the cerebral sclerosis encountered in geriatrics; epileptic vertigo attributable to cranial trauma; and metabolic encephalopathies.

Other aspects of the invention provide methods of making the polymorphs Form I and Form II are disclosed. In one embodiment, substantially pure Form I of Compound 1 is made by forming a solution of acetone and Compound 1, cooling the solution to result in a crystallized mass, and collecting the crystallized mass to yield substantially pure Form I. In another embodiment, substantially pure Form II of Compound 1 is made by forming a solution of methanol and Compound 1, cooling the homogenous solution to result in a crystallized mass, and collecting the crystallized mass to yield substantially pure Form II. Specific embodiments of the invention include those wherein the solution of Compound 1 further comprises one or more other organic solvents, thereby making a combination homogeneous solution.

Another aspect of the invention provides a method of converting the polymorph Form II to the polymorph Form I. Specific embodiments of this aspect include: 1) exposing the polymorph Form II to a high energy, such as thermal energy or mechanical energy, process. Such processes include: 1) exposing the polymorph Form II to an elevated temperature for a sufficient period of time to convert the polymorph Form II to the polymorph Form I; 2) milling or grinding the polymorph Form II to form the polymorph Form I; 3) dissolving the polymorph Form II in acetone (or a combination of acetone and one or more other solvents) to form a solution, cooling the solution to form a crystallized mass, and collecting the crystallized mass to yield substantially pure Form I; and/or 4) heating the polymorph Form II above its melting point to form a molten mass, and cooling the molten mass to form the polymorph Form I. This aspect of the invention can also be used to purify lots of polymorph Form I that contain unacceptable amounts of the polymorph Form II by subjecting impure polymorph Form I to one or more of the above-described specific embodiments of this aspect of the invention.

Compositions are also disclosed containing substantially pure Form I or Form II in combination with a pharmaceutically acceptable carrier. Such compositions may assume a variety of forms, including pills, tablet and capsules for oral administration.

These and other aspects of this invention will be apparent upon reference to the following detailed description and attached figures. To that end, certain patent and other documents are cited herein to more specifically set forth various aspects of this invention. Each of these documents is hereby incorporated by reference in its entirety.

DETAILED DESCRIPTION OF THE INVENTION

Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. In this case, the metastable form, although less stable, may exhibit properties desirable over those of the stable form, such as enhanced solubility or better oral bioavailability.

In the practice of this invention, two different polymorphs of the Compound 1 have been discovered and methods of their preparation have been developed. It has surprisingly been found that substantially pure polymorphic forms of Compound 1 are particularly advantageous with regard to use of the same as a pharmaceutical agent.

The present inventors have discovered the polymorph Form I, which has a "high" melting point of about 196° C., and the polymorph Form II, which has a "low" melting point of about 176° C., as measured by a TA 2920 Modulated Differential Scanning Calorimeter (TA Instruments, New Castle, Del.), at a scan rate of 10° C. per minute.

Figure 1:
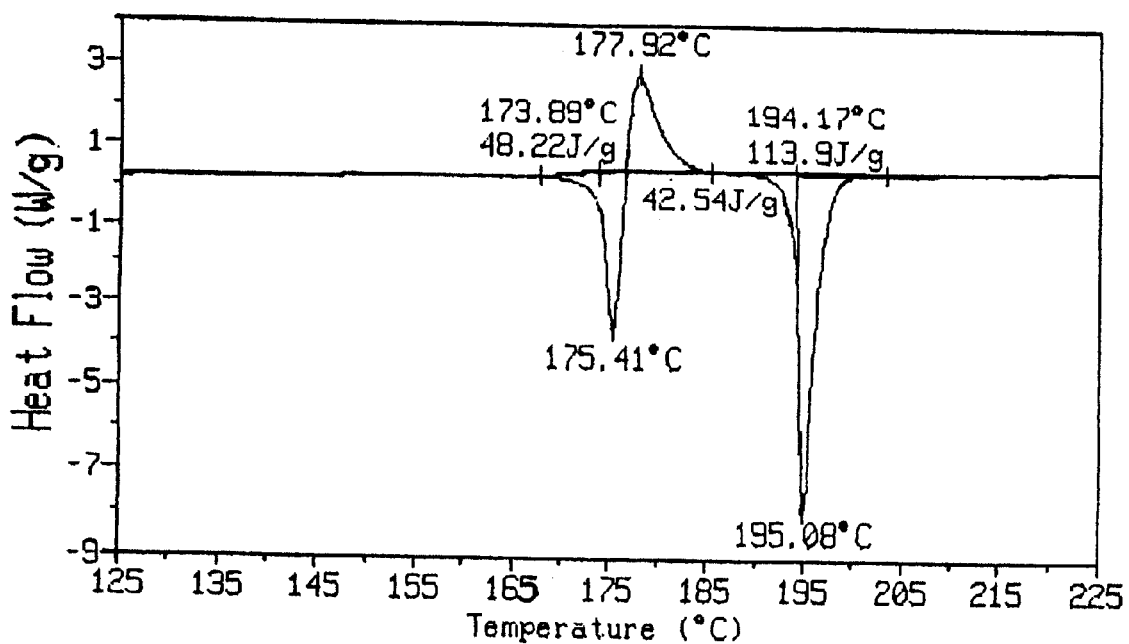
FIG. 1 is a Differential Scanning Calorimetry (DSC) thermogram of (Compound 1) as prepared by conventional techniques.

FIG. 1 is a Differential Scanning Calorimetry (DSC) thermogram (as measured by the instrument noted above) of Compound 1 made according to the prior art (see Example 1). As illustrated in FIG. 1, Compound 1 exhibits endotherms at 175.41° C. and 195.08° C., and an exotherm at 177.93° C., establishing the presence of both the high melting point, Form I polymorph, and the low melting point, Form II polymorph.

Figure 2:
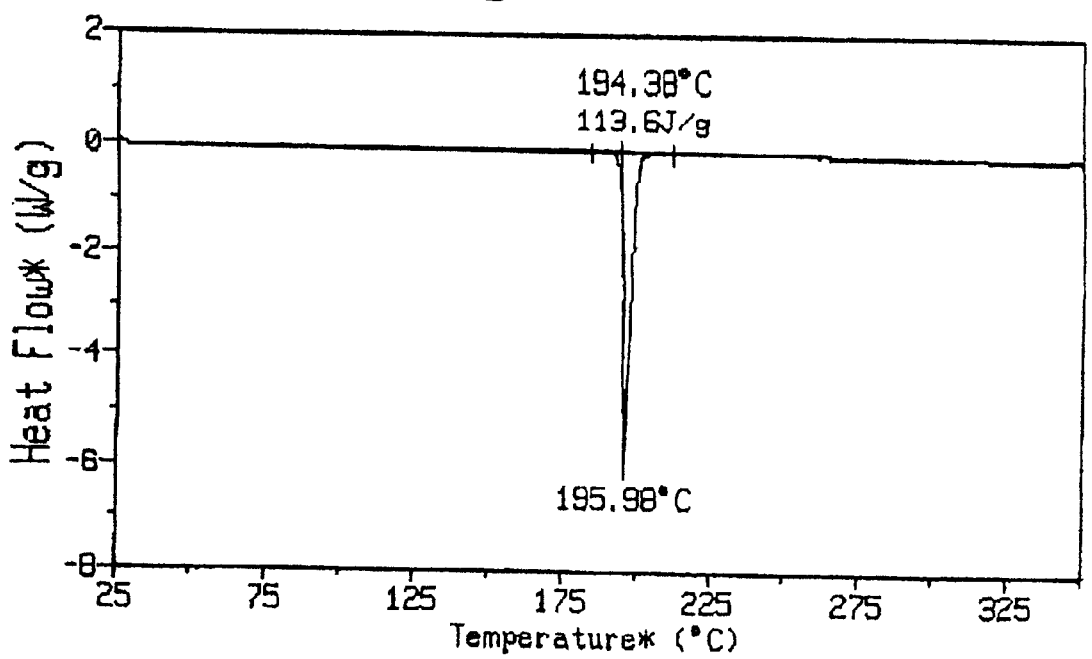
FIG. 2 is a DSC thermogram of the "high" melting point polymorph of Compound 1, referred to herein as Form I.
Figure 3:
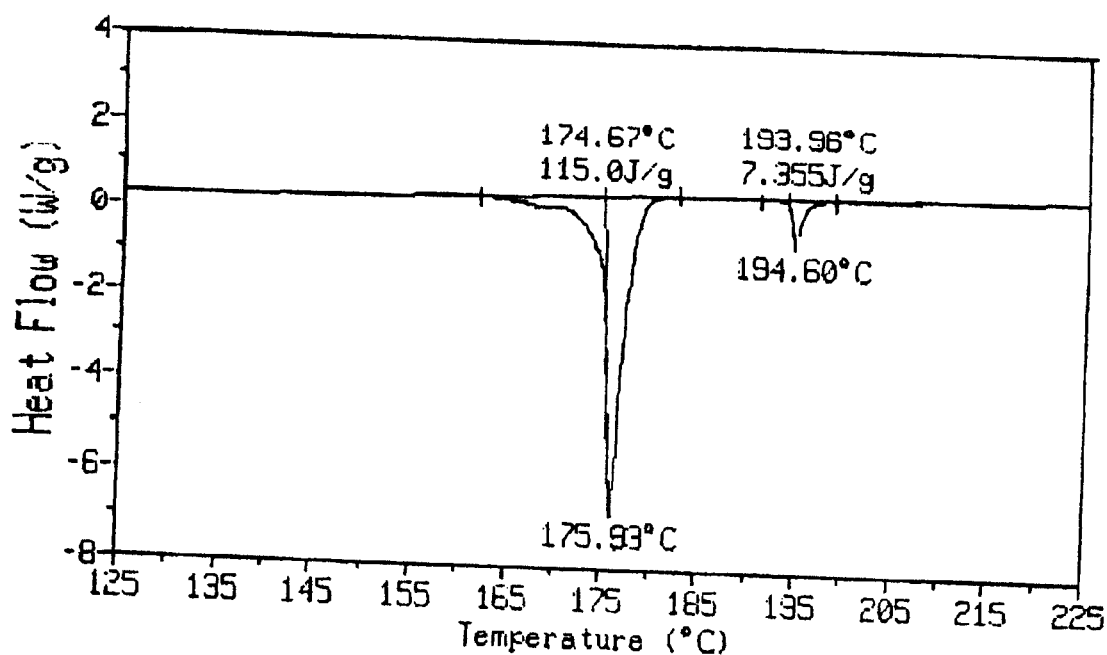
FIG. 3 is a DSC thermogram of the "low" melting point polymorph of Compound 1, referred to herein as Form II.

FIG. 2 is a DSC thermogram of substantially pure polymorph Form I made according to the process of the invention. FIG. 1 is a DSC thermogram of substantially pure polymorphic Form II. As illustrated in FIG. 2, Form I exhibits a predominant endotherm at 195.98° C., while FIG. 3 shows that Form II exhibits a predominant endotherm at 175.93° C. (the minor endotherm at 194.6° C. in FIG. 3 is due to the presence of Form I in an amount of about 6% by weight).

Depending upon the rate of heating, i.e. the scan rate, at which the DSC analysis is conducted, the calibration standard used, instrument calibration, the relative humidity and upon the chemical purity, the endotherms of the respective Forms I and II may vary by about 0.01–100° C., or about 0–5° C., above or below the endotherms depicted in the drawings. For any given sample, the observed endotherm may also differ from instrument to instrument; however, it will generally be within the ranges defined herein provided the instruments are calibrated similarly.

The polymorphs Form I and Form II differ in their crystal structure as determined by single-crystal X-ray crystallography. The data relating to the single-crystal X-ray crystallography spectrum for Form I is presented in the following Tables 1–6, as obtained on a Picker four-circle goniostat equipped with a Furnas Monochromator (HOG crystal), modified by addition of stepping motors (Slo-Syn) on each of the four axes, and a fifth motor drives a 20-position filter/attenuator wheel.

TABLE 1

Crystal Parameters of Form I

| | |
|---|---|
| Crystal Dimensions were: | 0.12 × 0.05 × 0.015 mm. |
| Space Group: | P1bar |
| Cell Dimensions | a = 9.148(12) |
| (at −160.C; 630 peaks): | b = 9.381(19) |
| | c = 12.254(26) |
| | alpha = 95.25(2) |
| | beta = 97.56(5) |
| | gamma = 117.25(3) |
| Z (Molecules/cell): | 2 |
| Volume: | 912.89 |
| Calculated Density: | 1.370 |
| Wavelength: | 0.71073 |
| Molecular Weight: | 376.44 |
| F(000): | 392 |
| Linear Absorption Coefficient: | 2.005 |

TABLE 2

Fractional Coordinates and Isotropic Thermal Parameters for Form 1

| Atom | x | y | z | Biso |
|---|---|---|---|---|
| S(1) | 4836(2) | 921(2) | 3413(2) | 32 |
| C(2) | 5144(8) | 1169(9) | 2068(6) | 32 |
| C(3) | 6077(8) | 2759(10) | 1966(6) | 33 |
| C(4) | 6616(7) | 3861(8) | 3004(6) | 21 |
| C(5) | 6063(7) | 3036(7) | 3886(6) | 20 |
| C(6) | 6208(7) | 3615(8) | 5088(6) | 18 |
| O(7) | 5357(5) | 2619(6) | 5672(4) | 30 |
| C(8) | 7312(7) | 5328(8) | 5645(5) | 19 |
| C(9) | 7089(7) | 5950(8) | 6673(6) | 21 |
| N(10) | 8255(6) | 7498(7) | 7116(4) | 20 |
| N(11) | 9300(6) | 7916(6) | 6339(4) | 16 |
| C(12) | 10768(7) | 9407(8) | 6460(6) | 17 |
| C(13) | 11659(7) | 9532(8) | 5616(6) | 20 |
| C(14) | 11104(8) | 8186(9) | 4734(6) | 22 |
| N(15) | 9700(6) | 6762(7) | 4626(5) | 22 |
| C(16) | 8790(8) | 6629(8) | 5438(6) | 18 |
| C(17) | 11234(8) | 10723(7) | 7419(6) | 18 |
| C(18) | 10044(8) | 11010(9) | 7893(6) | 26 |
| C(19) | 10561(8) | 12267(9) | 8784(7) | 37 |
| C(20) | 12266(8) | 13287(9) | 9266(6) | 33 |
| C(21) | 13451(8) | 13008(9) | 8797(6) | 26 |
| C(22) | 12967(7) | 11748(8) | 7883(6) | 20 |
| N(23) | 9232(8) | 12362(9) | 9356(6) | 51 |
| C(24) | 8642(9) | 11274(9) | 10235(6) | 31 |
| C(25) | 8492(12) | 13108(11) | 9028(8) | 57 |
| O(26) | 7218(6) | 13030(6) | 9441(4) | 36 |
| C(27) | 9108(9) | 14189(9) | 8095(7) | 31 |
| H(1) | 470* | 31* | 148* | 45 |
| H(2) | 643* | 313* | 128* | 44 |
| H(3) | 732* | 500* | 310* | 34 |
| H(4) | 621* | 532* | 704* | 41 |
| H(5) | 1265* | 1051* | 562* | 32 |
| H(6) | 1174* | 834* | 415* | 36 |
| H(7) | 890* | 1034* | 758* | 39 |
| H(8) | 1267* | 1419* | 986* | 43 |
| H(9) | 1462* | 1365* | 908* | 43 |
| H(10) | 1379* | 1161* | 757* | 34 |
| H(11) | 873* | 1190* | 1091* | 46 |
| H(12) | 754* | 1044* | 997* | 46 |
| H(13) | 938* | 1082* | 1034* | 46 |
| H(14) | 1005* | 1416* | 787* | 40 |
| H(15) | 820* | 1376* | 748* | 40 |
| H(16) | 938* | 1525* | 840* | 40 |

Notes
1) Fractional coordinates are X 104 for non-hydrogen atoms and X 103 for hydrogen atoms. Biso values are X 10.
2) Isotropic values for those atoms refined anisotropically are calculated using the formula given by W. C. Hamilton, Acta Cryst., 12,609 (1959).
3) Parameters marked by an asterisk (*) were not varied.

TABLE 3

Bond Distances for Form I

| A | B | Distance |
|---|---|---|
| S(1) | C(2) | 1.728(9) |
| S(1) | C(5) | 1.763(7) |
| O(7) | C(6) | 1.263(8) |
| O(26) | C(25) | 1.306(12) |
| N(10) | N(11) | 1.392(7) |
| N(10) | C(9) | 1.352(8) |
| N(11) | C(12) | 1.404(7) |
| N(11) | C(16) | 1.415(8) |
| N(15) | C(14) | 1.343(8) |
| N(15) | C(16) | 1.357(9) |
| N(23) | C(19) | 1.514(10) |
| N(23) | C(24) | 1.530(10) |
| N(23) | C(25) | 1.234(9) |
| C(2) | C(3) | 1.365(10) |
| C(3) | C(4) | 1.434(9) |
| C(4) | C(5) | 1.400(10) |
| C(5) | C(6) | 1.490(10) |
| C(6) | C(8) | 1.483(9) |
| C(8) | C(9) | 1.418(9) |
| C(8) | C(16) | 1.421(9) |
| C(12) | C(13) | 1.380(9) |
| C(12) | C(17) | 1.486(9) |
| C(13) | C(14) | 1.428(9) |
| C(17) | C(18) | 1.415(10) |
| C(17) | C(22) | 1.424(8) |
| C(18) | C(19) | 1.387(10) |
| C(19) | C(20) | 1.409(9) |
| C(20) | C(21) | 1.404(10) |
| C(21) | C(22) | 1.412(9) |
| C(25) | C(27) | 1.584(13) |
| C(2) | H(1) | .921(7) |
| C(3) | H(2) | .978(8) |
| C(4) | H(3) | .945(7) |
| C(9) | H(4) | .954(7) |
| C(13) | H(5) | .949(6) |
| C(14) | H(6) | .961(7) |
| C(18) | H(7) | .940(6) |
| C(20) | H(8) | .958(7) |
| C(21) | H(9) | .952(6) |
| C(22) | H(10) | .950(7) |
| C(24) | H(11) | .943(8) |
| C(24) | H(12) | .939(7) |
| C(24) | H(13) | .954(7) |
| C(27) | H(14) | .953(8) |
| C(27) | H(15) | .942(7) |
| C(27) | H(16) | .937(8) |

TABLE 4

Bond Angles for Form I

| A | B | C | Angle |
|---|---|---|---|
| C(2) | S(1) | C(5) | 90.8(4) |
| N(11) | N(10) | C(9) | 102.8(5) |
| N(10) | N(11) | C(12) | 124.4(5) |
| N(10) | N(11) | C(16) | 112.7(5) |
| C(12) | N(11) | C(16) | 122.8(6) |
| C(14) | N(15) | C(16) | 115.9(6) |
| C(19) | N(23) | C(24) | 117.0(7) |
| C(19) | N(23) | C(25) | 121.6(10) |
| C(24) | N(23) | C(25) | 120.7(9) |
| S(1) | C(2) | C(3) | 113.1(5) |
| C(2) | C(3) | C(4) | 113.0(7) |
| C(3) | C(4) | C(5) | 111.7(6) |
| S(1) | C(5) | C(4) | 111.3(5) |
| S(1) | C(5) | C(6) | 116.1(5) |
| C(4) | C(5) | C(6) | 132.4(6) |
| O(7) | C(6) | C(5) | 119.4(6) |
| O(7) | C(6) | C(8) | 117.5(7) |
| C(5) | C(6) | C(8) | 123.1(6) |
| C(6) | C(8) | C(9) | 121.6(6) |

TABLE 4-continued

Bond Angles for Form I

| A | B | C | Angle |
|---|---|---|---|
| C(6) | C(8) | C(16) | 134.1(6) |
| C(9) | C(8) | C(16) | 104.1(6) |
| N(10) | C(9) | C(8) | 114.9(6) |
| N(11) | C(12) | C(13) | 114.7(6) |
| N(11) | C(12) | C(17) | 120.5(6) |
| C(13) | C(12) | C(17) | 124.8(6) |
| C(12) | C(13) | C(14) | 120.3(6) |
| N(15) | C(14) | C(13) | 124.6(6) |
| N(11) | C(16) | N(15) | 121.7(6) |
| N(11) | C(16) | C(8) | 105.5(6) |
| N(15) | C(16) | C(8) | 132.7(6) |
| C(12) | C(17) | C(18) | 123.3(6) |
| C(12) | C(17) | C(22) | 118.3(6) |
| C(18) | C(17) | C(22) | 118.4(6) |
| C(17) | C(18) | C(19) | 120.5(6) |
| N(23) | C(19) | C(18) | 117.8(6) |
| N(23) | C(19) | C(20) | 119.3(7) |
| C(18) | C(19) | C(20) | 122.3(7) |
| C(19) | C(20) | C(21) | 117.4(7) |
| C(20) | C(21) | C(22) | 121.8(6) |
| C(17) | C(22) | C(21) | 119.7(6) |
| O(26) | C(25) | N(23) | 121.1(11) |
| O(26) | C(25) | C(27) | 119.4(8) |
| N(23) | C(25) | C(27) | 119.4(10) |
| S(1) | C(2) | H(1) | 123.1(7) |
| C(3) | C(2) | H(1) | 123.7(9) |
| C(2) | C(3) | H(2) | 124.8(8) |
| C(4) | C(3) | H(2) | 122.0(7) |
| C(3) | C(4) | H(3) | 124.9(7) |
| C(5) | C(4) | H(3) | 123.4(7) |
| N(10) | C(9) | H(4) | 121.8(7) |
| C(8) | C(9) | H(4) | 123.3(7) |
| C(12) | C(13) | H(5) | 120.1(7) |
| C(14) | C(13) | H(5) | 119.7(7) |
| N(15) | C(14) | H(6) | 117.7(7) |
| C(13) | C(14) | H(6) | 117.6(7) |
| C(17) | C(18) | H(7) | 118.4(7) |
| C(19) | C(18) | H(7) | 121.1(7) |
| C(19) | C(20) | H(8) | 124.3(7) |
| C(21) | C(20) | H(8) | 118.2(7) |
| C(20) | C(21) | H(9) | 121.5(7) |
| C(22) | C(21) | H(9) | 116.7(7) |
| C(17) | C(22) | H(10) | 120.2(7) |
| C(21) | C(22) | H(10) | 120.1(6) |
| N(23) | C(24) | H(11) | 110.4(7) |
| N(23) | C(24) | H(12) | 110.3(6) |
| N(23) | C(24) | H(13) | 105.3(7) |
| H(11) | C(24) | H(12) | 111.0(8) |
| H(11) | C(24) | H(13) | 109.7(7) |
| H(12) | C(24) | H(13) | 110.0(7) |
| C(25) | C(27) | H(14) | 111.7(7) |
| C(25) | C(27) | H(15) | 106.5(7) |
| C(25) | C(27) | H(16) | 107.0(8) |
| H(14) | C(27) | H(15) | 109.9(8) |
| H(14) | C(27) | H(16) | 110.4(7) |
| H(15) | C(27) | H(16) | 111.3(7) |

TABLE 5

Anisotropic Thermal Parameters for Form I (bij form)

| Atom | b11 | b22 | b33 | b12 | b13 | b23 |
|---|---|---|---|---|---|---|
| S(1) | 79(3) | 80(4) | 77(2) | 22(3) | −5(2) | −3(2) |
| C(2) | 73(12) | 128(15) | 60(7) | 44(12) | −17(8) | −29(9) |
| C(3) | 86(13) | 143(16) | 56(7) | 32(12) | 24(8) | 7(9) |
| C(4) | 39(10) | 88(13) | 34(6) | 10(9) | −2(6) | −14(7) |
| C(5) | 50(10) | 37(11) | 58(7) | 19(9) | 1(7) | 2(7) |
| C(6) | 46(11) | 71(12) | 46(7) | 39(10) | 1(7) | 16(8) |
| O(7) | 83(8) | 96(9) | 54(5) | 6(7) | 5(5) | 30(6) |
| C(8) | 63(11) | 89(13) | 33(6) | 38(10) | 12(7) | 23(7) |
| C(9) | 64(11) | 87(13) | 45(7) | 35(10) | 16(7) | 34(8) |
| N(10) | 57(9) | 91(11) | 34(5) | 30(8) | 8(6) | 15(6) |
| N(11) | 53(9) | 70(10) | 29(5) | 26(8) | 1(6) | 4(6) |
| C(12) | 44(10) | 74(12) | 40(6) | 44(9) | −3(7) | 0(7) |
| C(13) | 49(10) | 77(12) | 42(6) | 25(10) | 7(7) | 12(7) |
| C(14) | 56(10) | 111(13) | 35(6) | 32(10) | 19(7) | 16(7) |
| N(15) | 57(9) | 85(10) | 46(6) | 31(9) | 2(6) | 10(6) |
| C(16) | 64(11) | 73(12) | 29(6) | 31(10) | 11(7) | 2(7) |
| C(17) | 69(11) | 45(11) | 34(6) | 18(9) | −1(7) | 0(7) |
| C(18) | 42(10) | 118(13) | 49(7) | 28(10) | −10(7) | −27(8) |
| C(19) | 56(11) | 151(16) | 92(8) | 62(11) | 17(8) | −47(10) |
| C(20) | 85(12) | 108(14) | 62(7) | 32(11) | −4(8) | −38(8) |
| C(21) | 63(11) | 111(14) | 54(7) | 47(10) | 4(7) | 3(8) |
| C(22) | 65(11) | 57(11) | 48(7) | 26(10) | 14(7) | 15(7) |
| N(23) | 158(14) | 162(15) | 100(8) | 77(13) | −24(9) | −50(9) |
| C(24) | 163(16) | 118(15) | 50(7) | 79(13) | 44(8) | 43(8) |
| C(25) | 230(23) | 143(18) | 94(11) | 110(17) | −119(13) | −84(11) |
| O(26) | 85(9) | 191(12) | 66(5) | 88(9) | 5(6) | −24(6) |
| C(27) | 122(14) | 138(15) | 60(7) | 77(12) | 28(8) | 41(9) |

Form of the anisotropic thermal parameter:
exp[−((h2)b11 + (k2)b22 + (l**2)b33 + 2hkb12 + 2hlb13 + 2klb23)]
All values are X 10**4.

TABLE 6

Anisotropic Thermal Parameters for Form I (Uij form)

| Atom | U11 | U22 | U33 | U12 | U13 | U23 |
|---|---|---|---|---|---|---|
| S(1) | 25(1) | 27(1) | 56(2) | 7(1) | −3(1) | −1(1) |
| C(2) | 23(4) | 44(5) | 44(5) | 15(4) | −8(4) | −15(4) |
| C(3) | 28(4) | 49(5) | 40(5) | 1(4) | 11(4) | 3(4) |
| C(4) | 13(3) | 30(4) | 25(4) | 3(3) | 1(3) | 7(4) |
| C(5) | 16(3) | 3(4) | 42(5) | 6(3) | 1(3) | 1(4) |
| C(6) | 15(4) | 24(4) | 33(5) | 13(3) | 1(3) | 8(4) |
| O(7) | 27(3) | 33(3) | 39(3) | 2(2) | 3(3) | 15(3) |
| C(8) | 20(4) | 31(4) | 24(4) | 3(3) | 6(3) | 1(4) |
| C(9) | 21(4) | 30(4) | 33(5) | 12(3) | 8(3) | 17(4) |
| N(10) | 18(3) | 31(4) | 25(4) | 10(3) | 4(3) | 8(3) |
| N(11) | 17(3) | 24(3) | 21(3) | 9(3) | 5(3) | 2(3) |
| C(12) | 14(3) | 25(4) | 29(5) | 15(3) | −1(3) | 5(3) |
| C(13) | 16(3) | 26(4) | 30(5) | 8(3) | 3(3) | 6(4) |
| C(14) | 18(3) | 38(5) | 25(5) | 1(3) | 9(3) | 8(4) |
| N(15) | 8(3) | 29(4) | 33(4) | 0(3) | 6(3) | 5(3) |
| C(16) | 21(3) | 25(4) | 21(4) | 0(3) | 5(3) | 1(3) |
| C(17) | 22(4) | 15(4) | 25(4) | 6(3) | 0(3) | 0(3) |
| C(18) | 13(3) | 40(5) | 35(5) | 9(3) | −5(3) | −13(4) |
| C(19) | 18(4) | 52(5) | 67(6) | 21(4) | 8(4) | −24(5) |
| C(20) | 27(4) | 37(5) | 45(5) | 11(4) | −2(4) | −19(4) |
| C(21) | 20(4) | 38(5) | 39(5) | 15(3) | 2(3) | 2(4) |
| C(22) | 21(4) | 20(4) | 35(5) | 9(3) | 7(3) | 8(4) |
| N(23) | 51(5) | 55(5) | 73(6) | 26(4) | 42(4) | −25(4) |
| C(24) | 53(5) | 40(5) | 36(5) | 26(4) | 21(4) | 21(4) |
| C(25) | 74(7) | 49(6) | 68(8) | 36(6) | −57(6) | 2(6) |
| O(26) | 27(3) | 65(4) | 48(4) | 29(3) | 3(3) | −12(3) |
| C(27) | 39(4) | 47(5) | 43(5) | 25(4) | 4(4) | 21(4) |

Similarly, the data relating to the single-crystal X-ray crystallography spectrum for Form II is presented in the following Tables 7–12.

TABLE 7

Crystal Parameters of Form II

| | |
|---|---|
| Crystal Dimensions: | .35 × .20 × .12 mm. |
| Space Group: | P2/a1 |
| Cell Dimensions | a = 6.807(5) |
| (at −176° C.; 22 reflections): | b = 29.581(19) |
| | c = 9.053(6) |
| | beta = 99.62(2) |

TABLE 7-continued

Crystal Parameters of Form II

| | |
|---|---|
| Z (Molecules/cell): | 4 |
| Volume: | 1797.18 |
| Calculated Density: | 1.391 |
| Wavelength: | 0.71069 |
| Molecular Weight: | 376.44 |
| Linear Absorption Coefficient: | 2.037 |

TABLE 8

Fractional Coordinates and Isotropic Thermal Parameters for Form II

| Atom | x | y | z | Biso |
|---|---|---|---|---|
| S(1) | 4378(3) | 1289(1) | 6595(2) | 35 |
| C(2) | 5151(12) | 794(2) | 5925(8) | 34 |
| C(3) | 6289(12) | 869(3) | 4840(8) | 34 |
| C(4) | 6493(11) | 1329(3) | 4514(7) | 26 |
| C(5) | 5536(11) | 1608(2) | 5382(7) | 21 |
| C(6) | 5313(11) | 2094(2) | 5514(8) | 23 |
| O(7) | 4801(8) | 2253(2) | 6651(5) | 35 |
| C(8) | 5607(10) | 2418(2) | 4323(7) | 20 |
| C(9) | 5589(10) | 2878(2) | 4557(7) | 21 |
| N(10) | 5744(8) | 3129(2) | 3361(6) | 21 |
| N(11) | 5862(8) | 2809(2) | 2283(6) | 19 |
| C(12) | 5963(10) | 2903(2) | 792(7) | 19 |
| C(13) | 6030(10) | 2539(2) | −105(7) | 20 |
| C(14) | 5930(10) | 2102(2) | 485(7) | 20 |
| N(15) | 5840(9) | 2011(2) | 1908(6) | 20 |
| C(16) | 5765(11) | 2369(2) | 2798(7) | 21 |
| C(17) | 6018(10) | 3376(2) | 253(7) | 16 |
| C(18) | 7129(10) | 3711(2) | 1090(7) | 23 |
| C(19) | 7262(11) | 4142(2) | 459(8) | 25 |
| C(20) | 6298(11) | 4232(2) | −961(8) | 24 |
| C(21) | 5168(11) | 3900(2) | −1767(7) | 24 |
| C(22) | 5008(11) | 3476(2) | −1159(7) | 21 |
| N(23) | 8335(11) | 4496(2) | 1368(7) | 33 |
| C(24) | 7149(12) | 4796(3) | 2197(9) | 42 |
| C(25) | 10210(15) | 4577(3) | 1391(8) | 36 |
| O(26) | 11062(8) | 4913(2) | 2093(5) | 34 |
| C(27) | 11428(11) | 4247(3) | 569(8) | 33 |
| H(1) | 484* | 50* | 626* | 44 |
| H(2) | 688* | 63* | 435+ | 44 |
| H(3) | 722* | 144* | 377* | 36 |
| H(4) | 548* | 301* | 550* | 31 |
| H(5) | 614* | 258* | −113* | 29 |
| H(6) | 593* | 185* | −18* | 30 |
| H(7) | 779* | 365* | 208* | 33 |
| H(8) | 641* | 452* | −139* | 34 |
| H(9) | 449* | 396* | −275* | 34 |
| H(10) | 420* | 325* | −172* | 31 |
| H(11) | 761* | 477* | 324* | 52 |
| H(12) | 730* | 510* | 191* | 52 |
| H(13) | 579* | 471* | 198* | 52 |
| H(14) | 1144* | 396* | 101* | 43 |
| H(15) | 1085* | 423* | −46* | 43 |
| H(16) | 1276* | 435* | 65* | 43 |

Note
1) Fractional coordinates are X 104 for non-hydrogen atoms and X 103 for hydrogen atoms. Biso values are X 10.
2) Isotropic values for those atoms refined anisotropically are calculated using the formula given by W. C. Hamilton, Acta Cryst. 12:609 (1959)
3) Parameters marked by an asterisk (*) were not varied.

TABLE 9

Bond Distances for Form II

| A | B | Distance |
|---|---|---|
| S(1) | C(2) | 1.703(8) |
| S(1) | C(5) | 1.734(6) |
| O(7) | C(6) | 1.233(7) |
| O(26) | C(25) | 1.267(9) |
| N(10) | N(11) | 1.373(6) |
| N(10) | C(9) | 1.332(7) |
| N(11) | C(12) | 1.391(7) |
| N(11) | C(16) | 1.389(7) |
| N(15) | C(14) | 1.328(7) |
| N(15) | C(16) | 1.336(8) |
| N(23) | C(19) | 1.451(9) |
| N(23) | C(24) | 1.486(8) |
| N(23) | C(25) | 1.295(9) |
| C(2) | C(3) | 1.366(9) |
| C(3) | C(4) | 1.405(9) |
| C(4) | C(5) | 1.377(9) |
| C(5) | C(6) | 1.453(9) |
| C(6) | C(8) | 1.480(8) |
| C(8) | C(9) | 1.379(8) |
| C(8) | C(16) | 1.410(8) |
| C(12) | C(13) | 1.353(8) |
| C(12) | C(17) | 1.484(8) |
| C(13) | C(14) | 1.405(8) |
| C(17) | C(18) | 1.392(8) |
| C(17) | C(22) | 1.379(9) |
| C(18) | C(19) | 1.406(9) |
| C(19) | C(20) | 1.369(9) |
| C(20) | C(21) | 1.379(9) |
| C(21) | C(22) | 1.379(8) |
| C(25) | C(27) | 1.548(10) |
| C(2) | H(1) | .950(7) |
| C(3) | H(2) | .950(7) |
| C(4) | H(3) | .949(6) |
| C(9) | H(4) | .950(6) |
| C(13) | H(5) | .950(6) |
| C(14) | H(6) | .950(6) |
| C(18) | H(7) | .950(7) |
| C(20) | H(8) | .950(6) |
| C(21) | H(9) | .950(7) |
| C(22) | H(10) | .949(7) |
| C(24) | H(11) | .952(8) |
| C(24) | H(12) | .949(8) |
| C(24) | H(13) | .948(8) |
| C(27) | H(14) | .952(8) |
| C(27) | H(15) | .949(8) |
| C(27) | H(16) | .952(7) |

TABLE 10

Bond Angles for Form II

| A | B | C | Angle |
|---|---|---|---|
| C(2) | S(1) | C(5) | 92.4(4) |
| N(11) | N(10) | C(9) | 102.4(4) |
| N(10) | N(11) | C(12) | 124.7(5) |
| N(10) | N(11) | C(16) | 113.4(5) |
| C(12) | N(11) | C(16) | 121.8(6) |
| C(14) | N(15) | C(16) | 116.0(5) |
| C(19) | N(23) | C(24) | 116.9(7) |
| C(19) | N(23) | C(25) | 123.0(7) |
| C(24) | N(23) | C(25) | 119.9(8) |
| S(1) | C(2) | C(3) | 111.3(6) |
| C(2) | C(3) | C(4) | 113.3(7) |
| C(3) | C(4) | C(5) | 112.9(6) |
| S(1) | C(5) | C(4) | 110.1(5) |
| S(1) | C(5) | C(6) | 114.9(5) |
| C(4) | C(5) | C(6) | 135.0(6) |
| O(7) | C(6) | C(5) | 119.6(6) |
| O(7) | C(6) | C(8) | 116.9(6) |
| C(5) | C(6) | C(8) | 123.4(6) |
| C(6) | C(8) | C(9) | 121.4(6) |
| C(6) | C(8) | C(16) | 133.5(6) |
| C(9) | C(8) | C(16) | 104.9(6) |

TABLE 10-continued

Bond Angles for Form II

| A | B | C | Angle |
|---|---|---|---|
| N(10) | C(9) | C(8) | 115.0(5) |
| N(11) | C(12) | C(13) | 115.8(6) |
| N(11) | C(12) | C(17) | 121.0(6) |
| C(13) | C(12) | C(17) | 123.1(6) |
| C(12) | C(13) | C(14) | 119.7(6) |
| N(15) | C(14) | C(13) | 124.6(6) |
| N(11) | C(16) | N(15) | 122.1(6) |
| N(11) | C(16) | C(8) | 104.4(6) |
| N(15) | C(16) | C(8) | 133.5(6) |
| C(12) | C(17) | C(18) | 122.3(6) |
| C(12) | C(17) | C(22) | 118.2(6) |
| C(18) | C(17) | C(22) | 119.4(6) |
| C(17) | C(18) | C(19) | 119.4(7) |
| N(23) | C(19) | C(18) | 119.0(7) |
| N(23) | C(19) | C(20) | 120.6(7) |
| C(18) | C(19) | C(20) | 120.3(7) |
| C(19) | C(20) | C(21) | 119.7(6) |
| C(20) | C(21) | C(22) | 120.6(7) |
| C(17) | C(22) | C(21) | 120.4(7) |
| O(26) | C(25) | N(23) | 121.4(8) |
| O(26) | C(25) | C(27) | 119.9(8) |
| N(23) | C(25) | C(27) | 118.7(8) |
| S(1) | C(2) | H(1) | 124.4(7) |
| C(3) | C(2) | H(1) | 124.3(8) |
| C(2) | C(3) | H(2) | 123.3(8) |
| C(4) | C(3) | H(2) | 123.4(8) |
| C(3) | C(4) | H(3) | 123.6(8) |
| C(5) | C(4) | H(3) | 123.5(7) |
| N(10) | C(9) | H(4) | 122.5(7) |
| C(8) | C(9) | H(4) | 122.6(7) |
| C(12) | C(13) | H(5) | 120.1(7) |
| C(14) | C(13) | H(5) | 120.2(6) |
| N(15) | C(14) | H(6) | 117.7(6) |
| C(13) | C(14) | H(6) | 117.7(6) |
| C(17) | C(18) | H(7) | 120.4(7) |
| C(19) | C(18) | H(7) | 120.2(7) |
| C(19) | C(20) | H(8) | 120.1(7) |
| C(21) | C(20) | H(8) | 120.2(8) |
| C(20) | C(21) | H(9) | 119.7(7) |
| C(22) | C(21) | H(9) | 119.7(7) |
| C(17) | C(22) | H(10) | 119.8(7) |
| C(21) | C(22) | H(10) | 119.8(7) |
| N(23) | C(24) | H(11) | 109.2(7) |
| N(23) | C(24) | H(12) | 109.5(7) |
| N(23) | C(24) | H(13) | 109.5(7) |
| H(11) | C(24) | H(12) | 109.4(7) |
| H(11) | C(24) | H(13) | 109.5(8) |
| H(12) | C(24) | H(13) | 109.7(8) |
| C(25) | C(27) | H(14) | 109.5(6) |
| C(25) | C(27) | H(15) | 109.7(7) |
| C(25) | C(27) | H(16) | 109.5(7) |
| H(14) | C(27) | H(15) | 109.4(7) |
| H(14) | C(27) | H(16) | 109.2(8) |
| H(15) | C(27) | H(16) | 109.4(7) |

TABLE 11

Anisotropic Thermal Parameters for Form II (bij form)

| Atom | b11 | b22 | b33 | b12 | b13 | b23 |
|---|---|---|---|---|---|---|
| S(1) | 215(6) | 10.5(3) | 100(3) | −7(1) | 45(4) | 14(1) |
| C(2) | 239(28) | 7(1) | 101(12) | −4(4) | −12(15) | 10(3) |
| C(3) | 267(30) | 7(1) | 92(12) | 4(4) | 9(16) | 4(3) |
| C(4) | 192(23) | 9(1) | 38(9) | −6(4) | −3(12) | 6(3) |
| C(5) | 113(22) | 7(1) | 55(10) | −9(4) | −9(12) | 9(3) |
| C(6) | 111(21) | 7(1) | 66(10) | −6(4) | 5(12) | 1(3) |
| O(7) | 292(18) | 12(1) | 54(7) | −7(3) | 74(9) | −5(2) |
| C(8) | 141(22) | 6(1) | 47(9) | 5(4) | 21(11) | −1(2) |
| C(9) | 118(21) | 9(1) | 35(9) | −5(4) | 19(11) | −4(3) |
| N(10) | 149(18) | 6(1) | 58(8) | 0(3) | 46(10) | −5(2) |
| N(11) | 110(17) | 7(1) | 49(8) | −6(3) | 34(9) | −5(2) |
| C(12) | 103(21) | 6(1) | 59(10) | 3(4) | 23(12) | 5(3) |
| C(13) | 145(22) | 6(1) | 50(9) | −4(4) | 63(12) | −3(2) |
| C(14) | 105(22) | 7(1) | 48(10) | 1(4) | 2(11) | −4(3) |
| N(15) | 154(18) | 4(1) | 61(8) | 6(3) | 32(10) | 2(2) |
| C(16) | 120(21) | 7(1) | 60(10) | 1(4) | 37(12) | 4(3) |
| C(17) | 79(20) | 5(1) | 54(10) | −4(3) | 25(12) | −4(2) |
| C(18) | 163(22) | 5(1) | 78(10) | −1(4) | 45(12) | −3(3) |
| C(19) | 152(23) | 6(1) | 85(11) | −3(4) | 17(13) | 1(3) |
| C(20) | 182(24) | 4(1) | 92(11) | 4(4) | 79(14) | 8(3) |
| C(21) | 168(24) | 7(1) | 73(11) | −7(4) | 62(13) | 1(3) |
| C(22) | 126(21) | 7(1) | 57(10) | 4(4) | 44(12) | −1(3) |
| N(23) | 185(21) | 9(1) | 112(11) | 4(4) | 50(12) | 5(3) |
| C(24) | 257(30) | 9(1) | 153(15) | 14(5) | 27(17) | −20(3) |
| C(25) | 273(32) | 11(1) | 76(12) | 0(5) | 61(17) | 17(3) |
| O(26) | 297(19) | 6(1) | 90(8) | −18(3) | 36(10) | −3(2) |
| C(27) | 60(24) | 13(1) | 89(11) | −11(4) | 68(14) | −11(3) |

Note:
Form of the anisotropic thermal parameter:
exp[−((h2)b11 + (k2)b22 + (l**2)b33 + 2hkb12 + 2hlb13 + 2klb23)]
All values are X 10**4.

TABLE 12

Anisotropic Thermal Parameters for Form II (Uij form)

| Atom | U11 | U22 | U33 | U12 | U13 | U23 |
|---|---|---|---|---|---|---|
| S(1) | 49(1) | 47(1) | 41(1) | −7(1) | 14(1) | 19(1) |
| C(2) | 55(6) | 29(5) | 41(5) | −4(4) | −5(5) | 14(4) |
| C(3) | 61(7) | 29(5) | 37(5) | 4(5) | 3(5) | 5(4) |
| C(4) | 44(5) | 39(5) | 15(4) | −6(5) | −1(4) | 8(4) |
| C(5) | 26(5) | 31(4) | 22(4) | −9(4) | −3(4) | 12(3) |
| C(6) | 25(5) | 33(5) | 27(4) | −6(4) | 2(4) | 2(4) |
| O(7) | 67(4) | 51(3) | 22(3) | −7(3) | 22(3) | −7(3) |
| C(8) | 32(5) | 25(4) | 19(4) | −5(4) | 6(3) | −1(3) |
| C(9) | 27(5) | 38(5) | 4(4) | −5(4) | 6(3) | −5(4) |
| N(10) | 34(4) | 25(3) | 23(3) | 0(3) | 14(3) | −7(3) |
| N(11) | 25(4) | 30(4) | 20(3) | −6(3) | 10(3) | −7(3) |
| C(12) | 23(5) | 26(4) | 24(4) | 3(4) | 7(4) | 6(4) |
| C(13) | 33(5) | 26(4) | 20(4) | −4(4) | 19(4) | −4(3) |
| C(14) | 24(5) | 31(5) | 19(4) | 1(4) | 1(3) | −5(4) |
| N(15) | 35(4) | 19(3) | 25(3) | 6(3) | 10(3) | 3(3) |
| C(16) | 27(5) | 31(5) | 24(4) | 1(4) | 11(4) | 5(4) |
| C(17) | 18(5) | 24(4) | 22(4) | 4(3) | 7(4) | −6(3) |
| C(18) | 37(5) | 21(4) | 32(4) | −1(4) | 14(4) | −3(4) |
| C(19) | 35(5) | 26(5) | 34(4) | −3(4) | 5(4) | 1(4) |
| C(20) | 42(6) | 19(4) | 37(5) | 4(4) | 24(4) | 1(3) |
| C(21) | 38(5) | 30(4) | 29(4) | −7(4) | 19(4) | 1(4) |
| C(22) | 29(5) | 31(5) | 23(4) | 4(4) | 13(4) | −1(3) |
| N(23) | 42(5) | 41(5) | 45(4) | 4(4) | 15(4) | 7(4) |
| C(24) | 59(7) | 39(5) | 62(6) | 14(5) | 8(5) | −26(4) |
| C(25) | 62(7) | 47(6) | 31(5) | 0(5) | 18(5) | 23(4) |
| O(26) | 68(4) | 27(3) | 36(3) | −18(3) | 11(3) | 4(3) |
| C(27) | 37(6) | 58(6) | 36(5) | −11(4) | 21(4) | −15(4) |

Note:
Form of the anisotropic thermal parameter:
exp[−2(pi**2)[(h* *2)((a*)2)U11 + (k2)((b*)2)U22 + (l2)((c*) **2)U33 + 2hk(a*)(b*)U12 + 2hl(a*)(c*)U13 + 2kl(b*)(c*)U23]]
All values are X 10**3

As evidenced by the above data, Compound 1 exists as a mixture or blend of polymorphic Forms I and II when made according to prior art techniques. It has been discovered that the above-described Form I is a higher melting, stable polymorph, while the Form II is the lower melting, metastable polymorph. In the context of this invention, Form I is considered to be "substantially pure" when Form II constitutes less than about 6% (by weight), less than about 3%, or less than about 1% of Form I. Form II is considered to be "substantially pure" when Form I constitutes less than about 20% (by weight), less than about 10%, or less than about 5% of Form II. In addition, a substantially pure form of either Form I or Form II will generally contain less than about 2% total impurities, less than about 1% water, and less than about 0.5% residual organic solvent.

Polymorphic Forms I and II of this invention may be obtained by crystallization, starting from Compound 1, with each polymorph resulting by crystallization from a different solvent. More specifically, Compound 1 may be obtained by the procedure disclosed in U.S. Pat. No. 4,521,422. Compound 1 is then crystallized from acetone as disclosed in Example 2 to yield Form I. Form II may also be obtained from Compound 1 as set forth above, but by crystallization from methanol as disclosed in Example 3.

Accordingly in another embodiment of this invention, a process is disclosed for preparing substantially pure Form I or Form II. The process involves the step of forming a homogenous solution of N-methyl-N-(3-{3-[2-thienylcarbonyl]-pyrazol-[1,5-α]-pyrimidin-7-yl}phenyl)acetamide in acetone (for production of Form I) or methanol (for production of Form II). A homogenous solution may be formed, for example, by mixing N-methyl-N-(3-{3-[2-thienylcarbonyl]-pyrazol-[1,5-α]-pyrimidin-7-yl}phenyl)acetamide with the appropriate solvent, followed by heating. The homogenous solution is then cooled, resulting in the crystallization of substantially pure Form I (if the solvent is acetone) or substantially pure Form II (if the solvent is methanol), which crystals arc then collected and dried (e.g., at 40° C. for a period of time, such as six or more hours). In order to effect preferential crystallization of one form over the other, the crystallization solvent can be seeded with crystals of the desired polymorph.

Depending upon the method in which the crystallization is conducted, the polymorph Form II may be obtained by crystallization from solvents such as methanol, acetonitrile, 1-butanol, diethyl ether, N,N-dimethylformamide (DMF), toluene, tetrahydrofuran (THF) and combinations thereof. Similarly, the polymorph Form I may be obtained by crystallization from solvents such as acetone, ethyl acetate, toluene and combinations thereof.

Large-scale processes of manufacture generally include transfer of a concentrated solution containing a desired compound. Accordingly, the Compound 1 may be added to the crystallization solvent as a solid or as a solution in a cosolvent, such as methylene chloride, methylene chloride/hexane or other organic solvent. The polymorph is then crystallized from acetone or methanol as desired to form the polymorph Form I or Form II, respectively.

The concentration of Compound 1 present in the cosolvent may vary from 0.1% wt. to saturation, 0.1% wt. to about 16%. The concentration of Compound 1 in the cosolvent will vary according to the temperature at which the cosolvent is held. Generally, wanner temperatures will provide more concentrated solutions of Compound 1.

A solution containing cosolvent and Compound 1 can be added to the crystallization solvent (for example, methanol or acetone) or the crystallization solvent can be added to the solution containing cosolvent and Compound 1. In either case, the solution containing Compound 1 is generally at ambient temperature or at an elevated temperature with respect to ambient temperature, and the crystallization solvent temperature is independently initially chilled (a temperature below ambient temperature), at ambient temperature, or at an elevated temperature (a temperature above ambient temperature). Alternatively, a solution containing Compound 1 and the cosolvent can undergo a solvent exchange and to form a solution or heterogeneous mixture of the crystallization solvent and Compound 1, as described in Example 4.

When conducting a crystallization, the crystallization solvent can be seeded with one or more crystals of a particular polymorph in order to promote formation of that particular crystal in the crystallization solvent. Seeding of the crystallization solvent is optional. In one embodiment, Compound 1 is dissolved in hot acetone. After cooling has begun, the crystallization solvent is seeded with crystals of the polymorph Form I. Alternatively, the seed crystals can be added once the crystallization solvent is saturated with Compound 1.

As used herein, the term "crystallization solvent" means a solvent or combination of solvents used to crystallize a polymorph of the Compound 1 to preferentially form the desired polymorph Form I of Form II. In one embodiment, the crystallization solvent used to crystallize the polymorph Form I comprises a major portion of acetone. In another embodiment, the crystallization solvent used to crystallize the polymorph Form II comprises a major portion of methanol. The crystallization solvent may also contain one or more of the herein-described cosolvents. The cosolvent can be present is a wide range of amounts depending upon the combination solvent system being used and the polymorph being produced.

Several organic solvents can be used as cosolvents in the crystallization of Form I or Form II from acetone or methanol, respectively. The cosolvent will generally be present in amounts small enough to ensure that it does not negatively interfere with the formation of the desired polymorph. Suitable cosolvents include polar solvent, nonpolar solvent, protic solvent, a protic solvent, acetone, methanol, ethanol, propanol, butanol, ethyl acetate, THF, DMF, diethyl ether, acetonitrile, toluene, dichloromethane, water, and combinations thereof.

Figure 4:
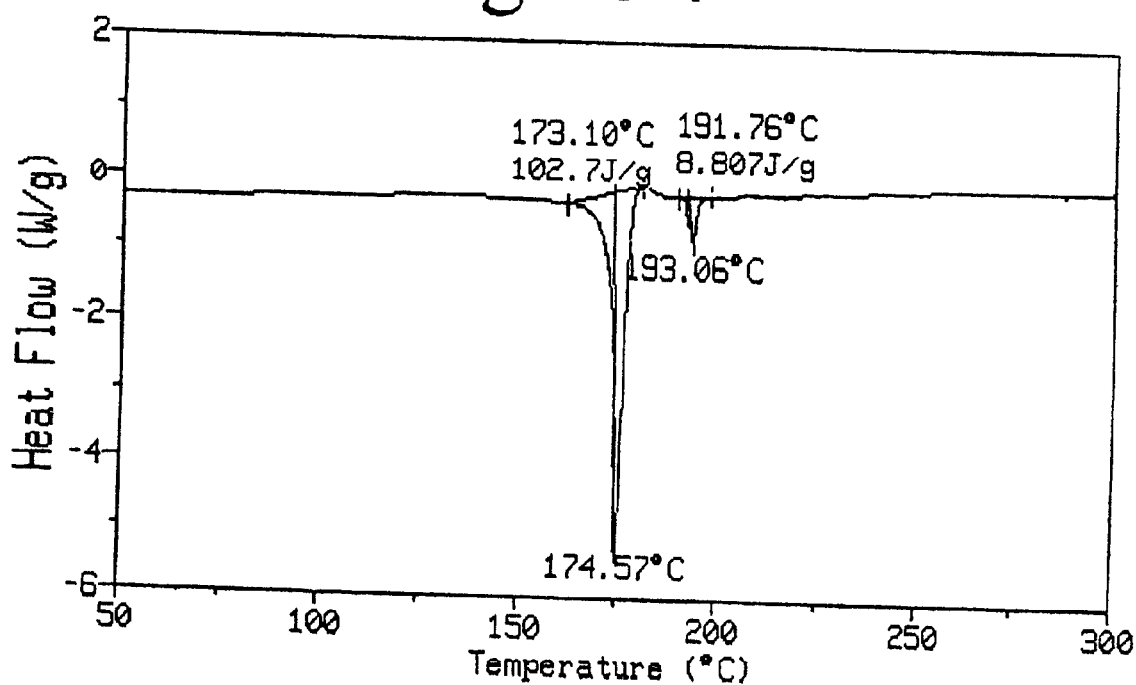
FIG. 4 is a DSC thermogram of the substantially pure polymorph Form II.
Figure 5:
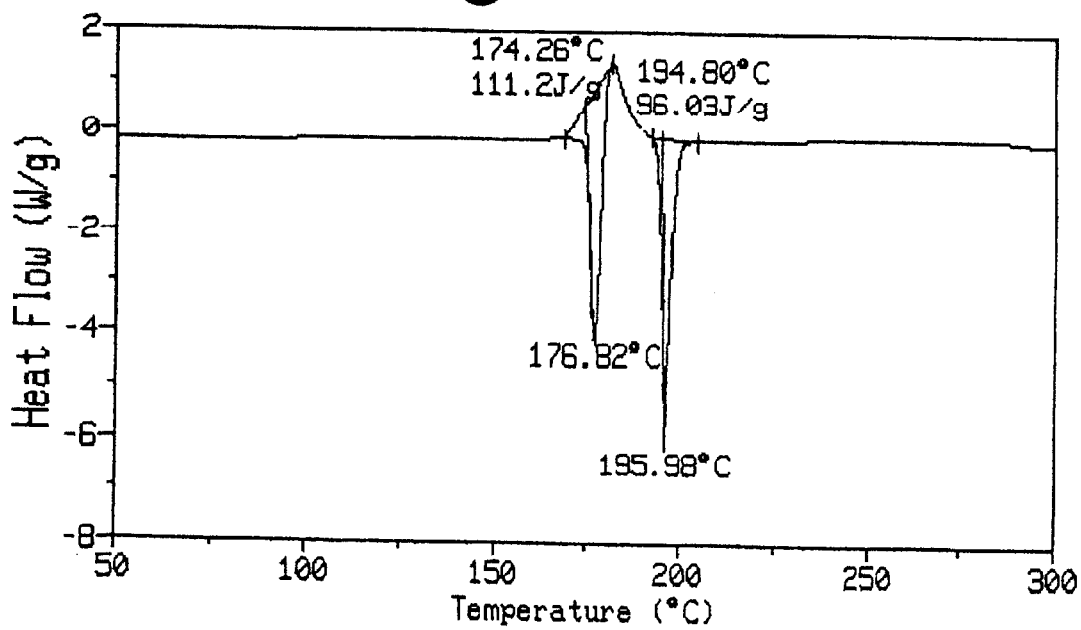
FIG. 5 is a DSC thermogram of an impure sample of the polymorph Form II containing a high level of Form I.
Figure 6:
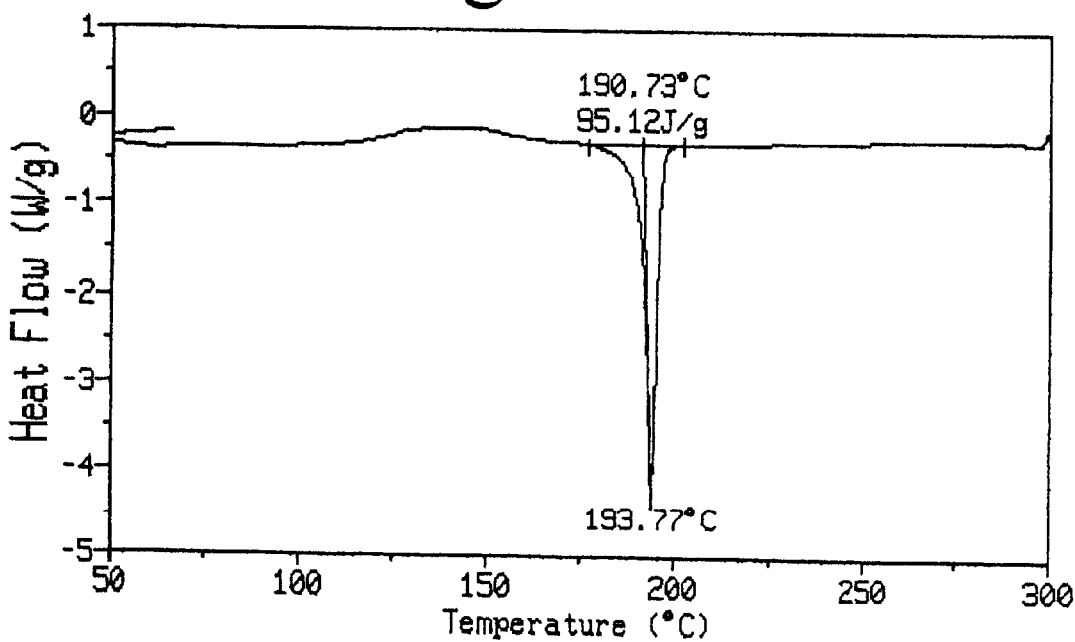
FIG. 6 is a DSC thermogram confirming the complete conversion of the polymorph Form II of FIG. 4 to the polymorph Form I by heating.

The polymorph Form I can be formed by heating the polymorph Form II for a sufficient period of time and at a temperature sufficient to effect the conversion. FIG. 4 depicts a DSC thermogram of a substantially pure polymorph Form II containing approximately 92% of Form II and approximately 8% of Form I. FIG. 5 depicts a DSC thermogram of a mixture of Compound 1 containing about 46% of polymorph Form I and about 54% of polymorph Form II. These amounts have been determined by quantitating the area within the endotherm peak for each respective polymorph, summing the respective areas, and calculating the relative percent of each peak with respect to the total area. The DSC thermograms of FIGS. 4 and 5 were obtained by employing the following procedure. A sample was heated from 15° C. to 300° C., at a scan rate of 10° C. per minute, in a DTC instrument and held at 300° C. for one minute. The sample was then cooled to 15° C. by lowering the temperature at a rate of 50° C. per minute DSC data were acquired during the temperature ramp up Another aliquot of the sample (Form II) of FIG. 4 was then treated in the DSC as follows to obtain the thermogram depicted in FIG. 6. The sample was heated from 15° C. to 185° C. at a scan rate of 10° C. per minute and then held at 185° C. for a period of 1 minute. After the minute, the sample was cooled to 15° C. by lowering the temperature at a rate of 50° C. per minute. After completion of this first heating cycle, the sample was heated from 15° C. to 300° C. at a scan rate of 10° C. per minute and then held at 300° C. for one minute. Finally, the sample was cooled to 15° C. by lowering the temperature at a rate of 50° C. per minute. DSC data were acquired during the second heating cycle of the DSC run. As a result of heating the sample to a temperature above the melting point of the polymorph Form II and subsequently cooling the sample, the impure polymorph Form II was converted to substantially pure polymorph Form I. Accordingly, by exposing the polymorph Form II to an elevated temperature, here 185° C. which is above the melting point of the polymorph Form II, for a sufficient period of time, here one minute, the polymorph Form II can be converted to the polymorph Form I. In a similar fashion, the mixture sample of FIG. 5 was treated as described immediately above. As a result, an impure sample of polymorph Form II containing approximately 46% of Form I and approximately 54% of Form II was converted to a substantially pure sample of the polymorph Form I (See FIG. 7).

Figure 8:
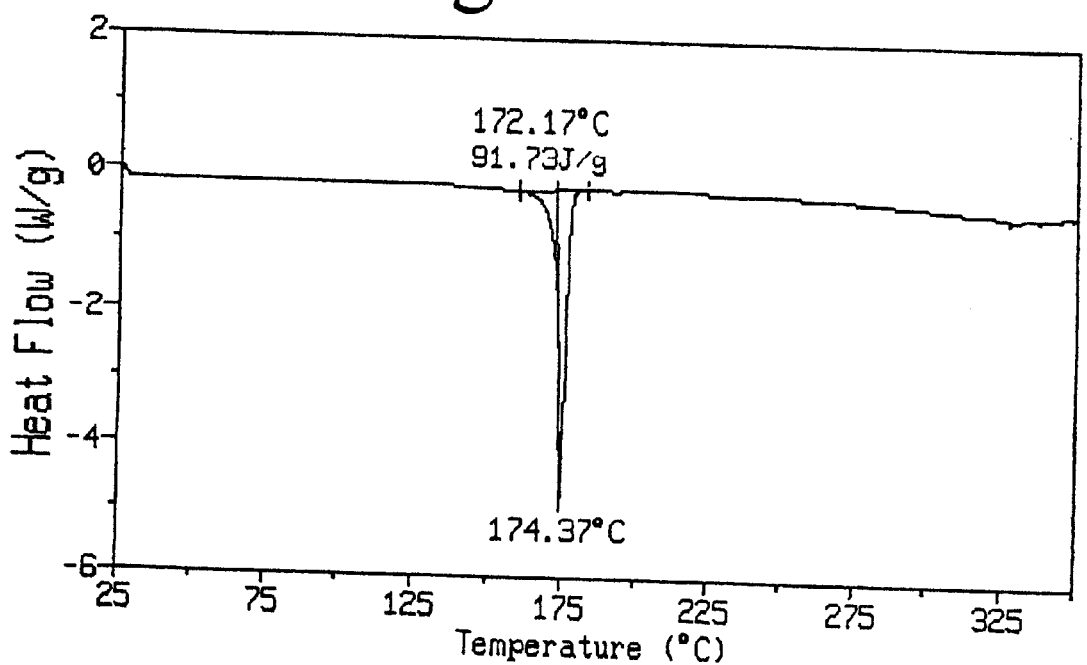
FIG. 8 is a DSC thermogram of the polymorph Form II prior to being exposed to high energy milling.
Figure 9:
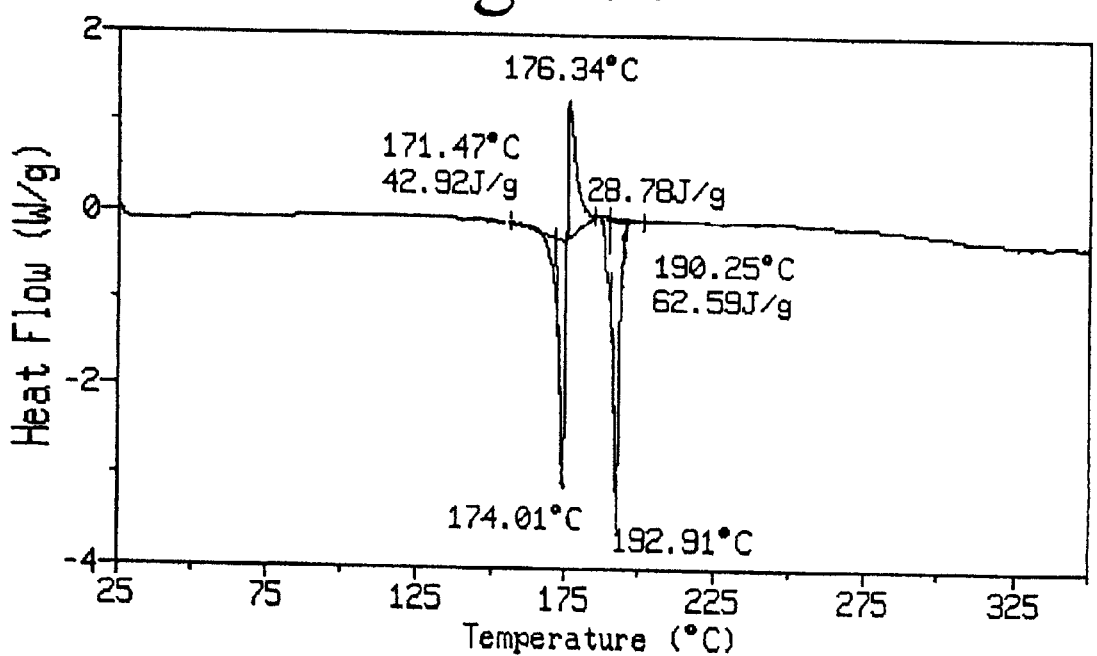
FIG. 9 is a DSC thermogram of the Compound 1 of FIG. 8 after the polymorph Form II has been exposed to a single pass of high energy milling.

Substantially pure Form I is also prepared by milling of Form II, or of Compound 1 that has been prepared according to known techniques. For example, milling of Form II in a fluid energy mill, jet mill, roller or ball mill, or other mechanical device to a mean particle size of approximately 1 micron to 15 microns will generally convert a portion or all of Form II to Form I. FIG. 8 is a DSC thermogram of the substantially pure polymorph Form II prior to being exposed to high energy milling and containing no detectable amounts of the polymorph Form I. By passing the polymorph Form II through a Retschmill having a 24-tooth, 1 mm screen, an impure mixture, containing significant amounts of the Form II(approximately 41%) and the Form I (about 59%), was formed, as depicted in FIG. 9. By passing the impure mixture repeatedly through a high energy mill, the polymorph Form II can be converted completely to the polymorph Form I. Likewise, an impure sample, batch or lot of the polymorph Form I containing unacceptable amounts of the polymorph Form II is converted to substantially pure polymorph Form I by milling the impure polymorph Form I one, two, three, four, five or more times.

The above-described process can be performed in combination. Accordingly, the polymorph Form II is converted to the polymorph Form I by heating the polymorph Form II, by milling the polymorph Form II, and/or by dissolving the polymorph Form II in an acetone containing solvent and crystallizing the polymorph Form I therefrom. In each case, the polymorph Form II can be pure, substantially pure or impure prior to conversion to the Form I.

The polymorph Form I is considered a heat stable form of Compound 1. By "heat stable" or "physically stable" is meant that the Form I is stable toward conversion to the polymorph Form II; although, it may be labile toward degradation to other compounds.

As the higher melting point polymorph, Form I has significant advantages over the polymorphic mixture of Compound 1 prepared according to known techniques. Specifically, Form I exhibits superior physical stability, thus allowing processing and manufacture of solid dosage forms without conversion to a different polymorphic form. This, in turn, enhances the milling and compaction properties of the drug substance.

In addition, the lower melting point polymorph, Form II, also has significant advantages over the polymorphic mixture of Compound 1 as prepared according to known techniques. Specifically, Form II exhibits superior water solubility over Form I and generally greater solubility in a range of organic solvents as compared to Form I (See Table 13). Form II is generally more soluble in polar and protic solvents than is Form I. Enhanced solubility of a compound will generally increase the bioavailability of that compound. When absorption of a drug is dissolution rate limited, use of the more soluble and faster dissolving form improves the rate and extent of bioavailability.

TABLE 13

Approximate Solubility of Form I and Form II in Various Solvents

| Solvent | Solubility (µg/mL) Form I | Solubility (µg/mL) Form II |
| --- | --- | --- |
| De-ionized water | 8.3 | 18.8 |
| Hexane | 41 | 50 |
| Diethyl ether | 80 | 51 |
| Isopropanol | 441 | 457 |
| Toluene | 997 | 645 |
| Ethanol, absolute (100%) | 1426 | 1722 |
| Methanol | 1740 | 1915 |
| Ethyl acetate | 1600 | 2160 |
| Acetone | 4842 | 6873 |
| Acetonitrile | 6246 | 8928 |
| Polyethylene Glycol 400, NF | 3259 | 10100 |
| Tetrahydrofuran | 9964 | 14740 |

For purposes of administration, a polymorph of this invention may be formulated as a pharmaceutical composition. Pharmaceutical compositions of the present invention comprise a polymorph and a pharmaceutically acceptable carrier, wherein the polymorph is present in the composition in an amount that is effective to treat the condition of interest. Preferably, the pharmaceutical compositions of the present invention include the polymorph in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain—in addition to the polymorph—diluents, dispersing and surface active agents, binders, and lubricants. One skilled in this art may further formulate the polymorph in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating conditions which benefit from administration of agents which possess anxiolytic, anti-anoxic, sleep-inducing, hypnotic, anticonvulsant, and/or skeletal muscle relaxant properties. Such condition include insomnia specifically, as well as sleep disorders generally and other neurological and psychiatric complaints, anxiety states, vigilance disorders, such as for combating behavioral disorders attributable to cerebral vascular damage and to the cerebral sclerosis encountered in geriatrics, epileptic vertigo attributable to cranial trauma, and for metabolic encephalopathies.

The methods of this invention include systemic administration of a polymorph as disclosed herein, preferably in the form of a pharmaceutical composition. As used herein, systemic administration encompasses both oral and parental methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions that may contain buffers, antioxidants, bacteriostats, and other additives commonly employed in such solutions.

The following examples are offered by way of illustration, not limitation.

EXAMPLE 1

Synthesis of Compound 1

This example illustrates the synthesis of Compound 1 by know techniques, Compound 1 as a mixture of polymorphic Forms I and Form II, as evidenced by the DSC thermogram of FIG. 1.

of anhydrous methanol was refluxed under nitrogen for 2 hours. The reaction mixture was cooled, concentrated and partitioned between water and dichloromethane. The dichloromethane layer was dried with anhydrous sodium sulfate, filtered and concentrated as to yield compound 4 as a dark yellow-orange oil (14.1 g, 93.3 mmol, 93%). GC/MS, m/z=151 at tR=8.30 min (100%). LC/MS,[M+H]=152.

α-[(Dimethylamino)methylene]-β-oxo-2-thiolphenepropanenitrile (5).

A mixture of Compound 4 (13.0 g, 86 mmol) and dimethylformamide dimethyl acetal (22.4 g, 188 mmol) was refluxed under nitrogen for 3 hrs. Solid precipitated from the reaction mixture. The reaction mixture was cooled, diluted with dichloromethane and ether (1:10, 200 mL). The solid

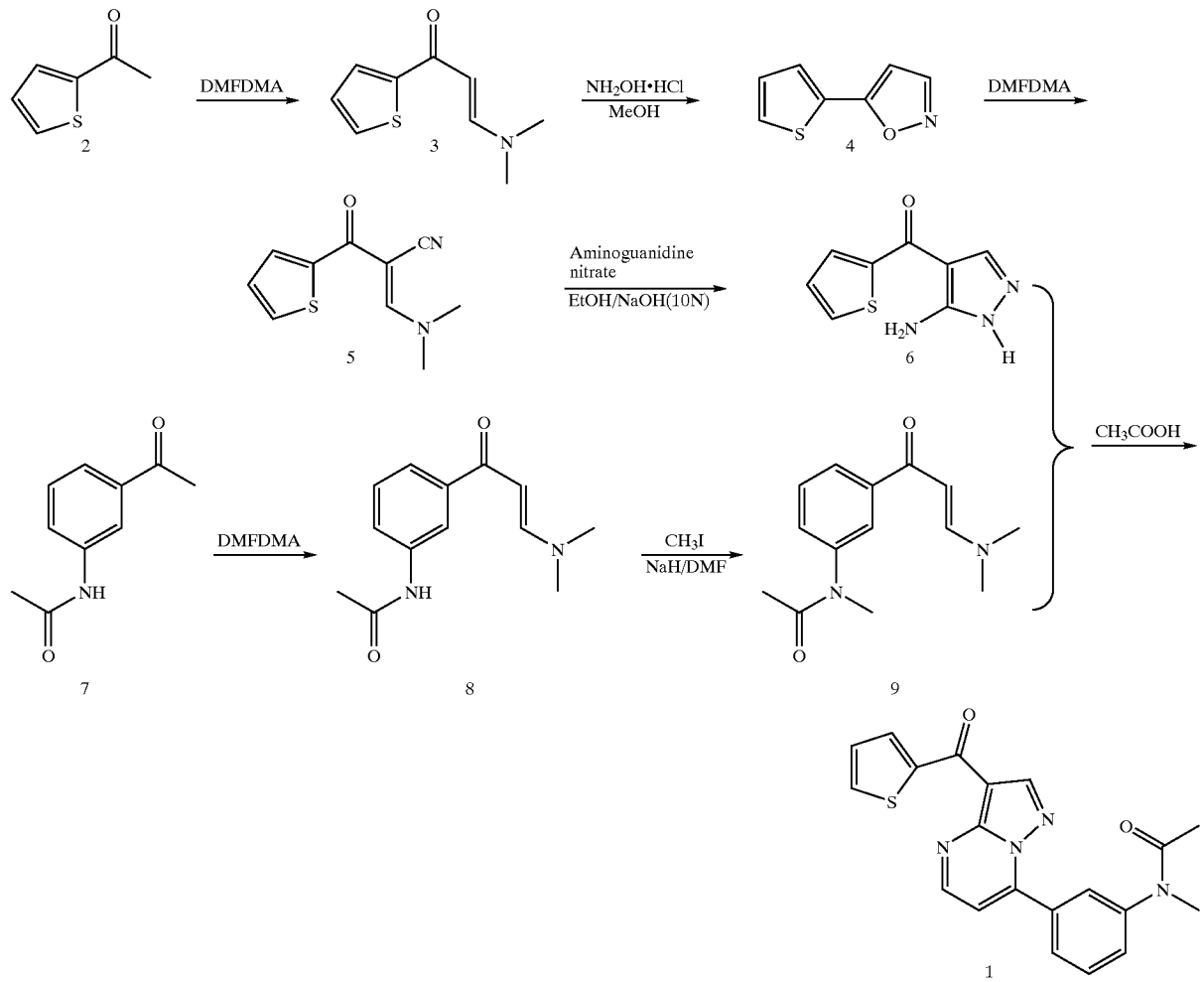

β-Dimethylamino-1-(2-thienyl)-2-propen-1-one (3).

A mixture of 2-acetylthiophene 2 (20.0 g, 159 mmol) and dimethylformamide dimethyl acetal (39 g, 327 mmol) was refluxed under nitrogen for 3 hours. The reaction mixture was cooled, concentrated to afford a dark orange solid. The solid was collected by filtration, triturated with a solution of dichloromethane and ether (1:10, 200 mL). Compound 3 was obtained as an orange solid (22.0 g, 121 mmol, 76%). GC/MS, m/z=181 at tR=11.83 min (100%). LC/MS,[M+H]=182.

5-(2-Thienyl)isoxazole (4).

A mixture of Compound 3 (18.1 g, 100 mmol) and hydroxylamine hydrochloride (7.0 g, 101 mmol) in 100 mL was collected by filtration, triturated with a solution of dichloromethane and ether (1:20, 100 mL). Compound 5 was obtained as an orange solid (13.5 g, 65.4 mmol, 76%). GC/MS, m/z=206 at tR=13.39 min (100%). LC/MS, [M+H]'=207.

(3-Amino-1H-pyrazol-4-yl)-2-thienylmethanone (6).

To a mixture of aminoguanidine nitrate (17.1, 125 mmol) and 5 (20.6 g, 100 mmol) in absolute ethanol (120 mL) was added 10N NaOH. The reaction mixture was refluxed for 6 hours and the solvents were removed at reduced pressure on a rotary evaporator. Water (250 mL) was added and an initial precipitate formed and was filtered (13.3 g, 68.8 mmol, 69%). On further standing, the aqueous layer deposited an additional quantity of die desired compound 6 (3.42 g, 17.7 mmol, 18%). Compound 6 was obtained as a tan solid (total 16.72 g, 86.5 mmol, 87%). GC/MS, m/z=193 at tR=13.67 min (100%). LC/MS,[M+H]'=194

N-[3-[3-(Dimethylamino)-1-oxo-2-propenyl]-phenyl]-acetamide (8).

A mixture of 3-acetamnidoacetophenone 7 (20 g, 112.9 mmol), dimethylformamide dimethyl acetal (40.3 g, 338.6 mmol) was refluxed under nitrogen for 1 hour. The reaction mixture was cooled, diluted with ethyl acetate (150 mL) and ether (150 mL). The solid was collected by filtration, triturated with a solution of ethyl acetate and hexane (1:1, 200 mL). Compound 8 was obtained as a red-orange solid (23.6 g, 101.6 mmol, 90%). GC/MS, m/z =232 at tR=15.11 min (100%). LC/MS,[M+H]'=233.

N-[3-[3-(Dimethylamino)-1-oxo-2-propenyl]-phenyl]-N-methyl acetamide (9).

To a suspension of compound 8 (22.07 g, 95 mmol) in anhydrous dimethylformamide (114 mL) under nitrogen in an ice bath was added sodium hydride (4.75 g, 119 mmol, 60% in mineral oil) and, within 15 minutes, the gas evolution had ceased. To the above reaction mixture was added a solution of methyl iodide (14.2 g, 99.8 mmol). The reaction mixture was stirred overnight and allowed to warm to room temperature. The reaction was triturated with hexane (3×150 mL) which was discarded. The reaction mixture was poured into ice water, extracted with dichloromethane (3×200 mL) which was dried with anhydrous sodium sulfate. The dry dichloromethane was concentrated to yield a solid which was triturated with a solution of ethyl acetate and hexane (1:1, 200 mL). Compound 9 was obtained as an orange solid (16.9 g, 68.6 mmol, 72%). GC/MS, m/z=246 at tR=14.63 min (100%). LC/MS,[M+H]'=247.

N-Methyl-N-[3-[3-(2-thienylcarbonyl)-pyrazolo[1,5-a]pyrimidin-7-yl]-phenyl]acetamide (Compound 1).

A mixture of compound 6 (11.0 g, 56.8 mmol) and compound 9 (14.0 g, 56.8 mmol) in glacial acetic acid (200 mL) was refluxed for 6 hrs. Evaporation of all volatiles on a rotary evaporator gave an oil residue, which was treated with dichloromethane (50 mL) and triturated with hexane (200 mL). The precipitate was collected by filtration and washed with 1:10 dichloromethane/hexane (100 mL). The product was dried in vacuo at 40° C. affording a mixture of Form I and Form II of Compound 1 as a pale yellow solid (16.28 g, 43.2 mmol, 76%). LC/MS,[M+H]'=377. 1H NMR (CDCl3,300 MHz), λ(ppm) 2.01(s, 3H), 3.36(s, 3H), 7.17 (d, 1H), 7.22 (dd, 1H), 7.48 (d, 1H), 7.67 (d, 1H), 7.72 (dd, 1H), 7.90–8.10 (M, 2H), 8.10 (dd, 1H), 8.73 (s, 1H), 8.85 (d, 1H).

EXAMPLE 2

Synthesis of Substantially Pure Form I

To 1.5 g of Compound 1 as prepared in Example 1 is added 100 mL of acetone. The solution is heated to reflux until the solution is homogeneous. The solution is quickly filtered through a glass-fritted funnel. The solution is allowed to gradually cool to room temperature, approximately 1 hour. The mixture is further cooled to 5° C. using an ice bath. The solid formed is collected by filtration and washed with 10 mL of cold acetone yielding 0.4 g of Form I. The mother liquor is concentrated to approximately 20 mL in vacuo. The solution is cooled to 5° C. and the solid is collected by filtration and washed with 10 mL of cold acetone affording an additional 0.5 g of Form I.

EXAMPLE 3

Synthesis of Substantially Pure Form II

To 1.4 g of Compound 1 as prepared in Example 1 is added 75 mL of methanol. The solution is heated to reflux until the solution is homogeneous. The solution is quickly filtered through a glass-fritted funnel. The solution is allowed to gradually cool to room temperature, approximately 1 hour. The mixture is further cooled to 5° C. using an ice bath. The solid formed is collected by filtration and washed with 10 mL of cold methanol yielding 0.5 g of Form II. The mother liquor is concentrated to approximately 10 mL in vacuo. The solution is cooled to 5° C. and the solid is collected by filtration and washed with 10 mL of cold methanol affording an additional 0.4 g of Form II.

EXAMPLE 4

Crystallization of Substantially Pure Form I from an Acetone/Cosolvent Mixture

To 38 g of Compound 1, as prepared in Example 1, was added 200 mL of dichloromethane. The mixture was stirred at 25° C. until the solution was homogeneous. The solution was filtered and 150 mL of acetone was added to the filtrate. The clear, yellow solution was heated to remove the dichloromethane distillate. During distillation, an additional 200 mL of acetone was slowly added to replace the volume of the dichloromethane. Following removal of dichloromethane as evidenced by the distillate temperature, distillation was continued until the solution volume was reduced to approximately 200 mL. Heating was discontinued and the warm solution seeded with pure crystals of polymorphic Form I. The solution was gradually cooled to 5° C. and stirring was continued for several hours. The slurry was filtered and the collected crystals washed with acetone and dried in vacuo at 40° C. affording 36 g of Compound 1 as polymorphic Form I.

EXAMPLE 5

Conversion of Form to Form II by Milling 5.5 g of Compound 1 consisting of approximately 100% polymorph Form II as shown in FIG. 8 was passed through a 30 mesh stainless steel screen and then through a Retschmill with a 24 tooth rotor and a 1 mm screen. 4.0 g (approximately 73%) of Compound 1 was recovered. The recovered material was approximately 59% Form I and 41% Form II as shown in FIG. 9. This procedure could be repeated to completely convert the Form II to the Form I.

EXAMPLE 6

Conversion of Polymorph Form II to Form I by Heating

An aliquot of substantially pure polymorph Form II (having the DSC thermogram of FIG. 4) was treated in a TA 2920 Modulated Differential Scanning Calorimeter (DSC) according to the following program: Equilibrate at 15° C.

Data storage off

Isothermal for 1 min

Ramp 10° C./min to 185° C.

Isothermal for 1 min

Ramp 50° C./min to 15° C.

Isothermal for 1 min

Data storage on

Ramp 10° C./min to 300° C.

Isothermal for 1 min

Data storage off

Ramp 50° C./min to 15° C.

The resulting thermogram (FIG. 6) showed substantially pure polymorph Form I (as evidenced by the endotherm at 193.77).

Figure 7:
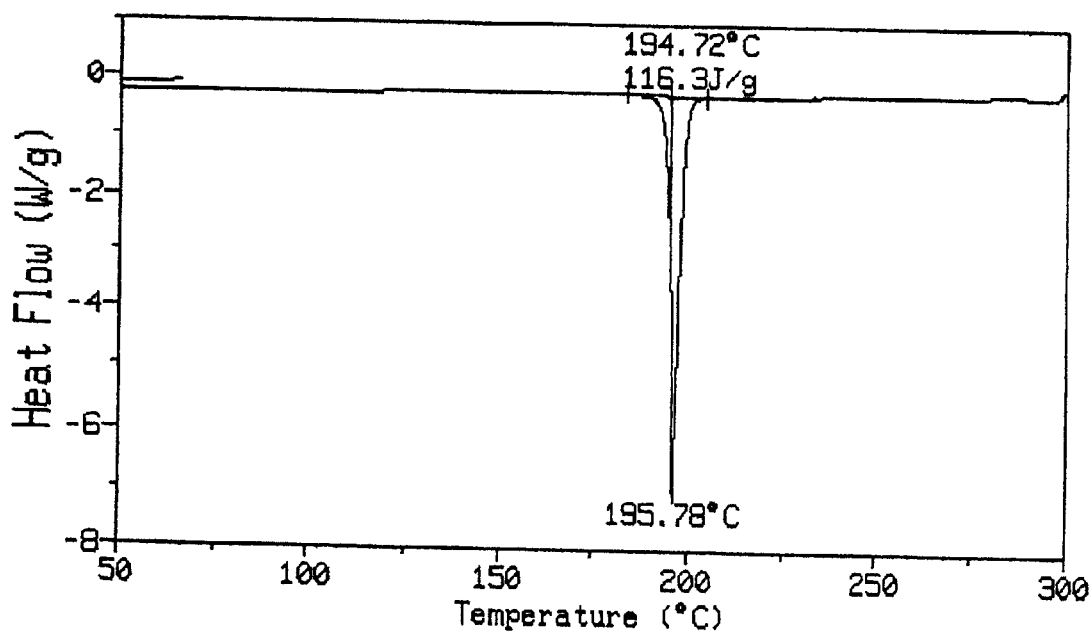
FIG. 7 is a DSC thermogram confirming the complete conversion of the polymorph Form II of FIG. 5 to the polymorph Form I by heating.

An aliquot of Compound 1 consisting of a mixture of Form I and Form II as shown in FIG. 5 was treated in the same manner, giving the thermogram of FIG. 7 which shows only Form I (endotherm at 195.78 only).

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

We claim:

1. A substantially pure polymorph Form I of N-methyl-N-(3-{3-[2-thienylcarbonyl]-pyrazol-[1,5-α]-pyrimidin-7-yl}phenyl)acetamide exhibiting a predominant endotherm at about 192–198° C. as measured by a Differential Scanning Calorimeter, and wherein said polymorph Form I comprises less than about 6% by weight of polymorph Form II.

2. The substantially pure polymorph Form I of claim 1, wherein said polymorph Form I comprises less than about 2% by weight impurities, less than about 1% by weight waters and less than about 0.5% by weight residual organic solvent.

3. The substantially pure polymorph Form I of claim 1, wherein said polymorph exhibits a predominant endotherm at about 195–197° C.

4. The substantially pure polymorph Form I of claim 1, wherein said polymorph has about 2 molecules per cell and is of the P1bar spare group as determined by single-crystal X-ray crystallography.

5. The substantially pure polymorph Form I of claim 1, wherein said polymorph has crystal dimensions of about 0.12 mm×0.05 mm×0.015 mm and a volume of about 913, as determined by single-crystal X-ray crystallography.

6. The substantially pure polymorph Form I of claim 1, wherein said polymorph has a calculated density of about 1.37, as determined by single-crystal X-ray crystallography.

7. The substantially pure polymorph Form I of claim 1, further characterized by the following single-crystal X-ray crystallography bond distances:

| A | B | Distance |
| --- | --- | --- |
| S(1) | C(2) | 1.728(9) |
| S(1) | C(5) | 1.763(7) |
| O(7) | C(6) | 1.263(8) |
| O(26) | C(25) | 1.306(12) |
| N(10) | N(11) | 1.392(7) |
| N(10) | C(9) | 1.352(8) |
| N(11) | C(12) | 1.404(7) |
| N(11) | C(16) | 1.415(8) |
| N(15) | C(14) | 1.343(8) |
| N(15) | C(16) | 1.357(9) |
| N(23) | C(19) | 1.514(10) |
| N(23) | C(24) | 1.530(10) |
| N(23) | C(25) | 1.234(9) |
| C(2) | C(3) | 1.365(10) |
| C(3) | C(4) | 1.434(9) |
| C(4) | C(5) | 1.400(10) |
| C(5) | C(6) | 1.490(10) |
| C(6) | C(8) | 1.483(9) |
| C(8) | C(9) | 1.418(9) |
| C(8) | C(16) | 1.421(9) |
| C(12) | C(13) | 1.380(9) |
| C(12) | C(17) | 1.486(9) |
| C(13) | C(14) | 1.428(9) |
| C(17) | C(18) | 1.415(10) |
| C(17) | C(22) | 1.424(8) |
| C(18) | C(19) | 1.387(10) |
| C(19) | C(20) | 1.409(9) |
| C(20) | C(21) | 1.404(10) |
| C(21) | C(22) | 1.412(9) |
| C(25) | C(27) | 1.584(13) |
| C(2) | H(1) | .921(7) |
| C(3) | H(2) | .978(8) |
| C(4) | H(3) | .945(7) |
| C(9) | H(4) | .954(7) |
| C(13) | H(5) | .949(6) |
| C(14) | H(6) | .961(7) |
| C(18) | H(7) | .940(6) |
| C(20) | H(8) | .958(7) |
| C(21) | H(9) | .952(6) |
| C(22) | H(10) | .950(7) |
| C(24) | H(11) | .943(8) |
| C(24) | H(12) | .939(7) |
| C(24) | H(13) | .954(7) |
| C(27) | H(14) | .953(8) |
| C(27) | H(15) | .942(7) |
| C(27) | H(16) | .937(8). |

8. The substantially pure polymorph Form I of claim 1, wherein said polymorph Form I comprises less than about 3% by weight of a polymorph Form II.

9. The substantially pure polymorph Form I of claim 1, wherein said polymorph Form I comprises less than about 1% by weight of a polymorph Form II.

10. A method for treating insomnia in a patient in need thereof, comprising administering to the patient an effective amount of substantially pure Form I of claim 1.

11. A method for inducing sleep in a patient in need thereof, comprising administering to the patient an effective amount of substantially pure Form I of claim 1.

12. A method for inducing sedation or hypnosis in a patient in need thereof, comprising administering to the patient an effective amount of substantially pure Form I of claim 1.

13. A method for inducing skeletal muscle relaxation in a patient in need thereof, comprising administering to the patient an effective amount of substantially pure Form I of claim 1.

14. A composition in the form of a pill, capsule or tablet, comprising substantially pure Form I of N-methyl N-(3-{3-[2-thienylcarbonal]-pyrazol-[1,5-α]-pyrimidin-7-yl}phenyl)acetamide according to claim 1 and a pharmaceutically acceptable carrier.

15. The composition of claim 14, wherein the Form I is present in a unit dosage form at an amount of about 0.1 to 250 mg.

* * * * *

UNITED STATES PATENT AND TRADEMARK OFFICE
CERTIFICATE OF CORRECTION

PATENT NO.    : 6,544,999 B2
DATED         : April 8, 2003
INVENTOR(S)   : William J. Thiele and Patrick B. O'Donnell It is certified that error appears in the above-identified patent and that said Letters Patent is hereby corrected as shown below:

<u>Title page,</u>
Item [54], "(PYRIMIDIN-9-YL}PHENYL)ACETAMIDE)" should read
-- PYRIMIDIN-7-YL}PHENYL)ACETAMIDE --

<u>Column 23,</u>
Line 28, "waters" should read -- water --
Line 35, "spare" should read -- space --

Signed and Sealed this

Twenty-eighth Day of October, 2003

JAMES E. ROGAN
*Director of the United States Patent and Trademark Office*